(12) United States Patent
Scopton et al.

(10) Patent No.: US 9,868,238 B1
(45) Date of Patent: Jan. 16, 2018

(54) MOLDABLE MATERIAL SHAPING SYSTEMS AND METHODS OF USE

(71) Applicant: Catheter Dynamics, Inc., Burlington, MA (US)

(72) Inventors: Paul M. Scopton, Winchester, MA (US); Yem Chin, Burlington, MA (US); Thomas R. Johnson, Milford, NH (US)

(73) Assignee: CATHETER DYNAMICS, INC., Burlington, MA (US)

( * ) Notice: Subject to any disclaimer, the term of this patent is extended or adjusted under 35 U.S.C. 154(b) by 46 days.

(21) Appl. No.: 14/194,367

(22) Filed: Feb. 28, 2014

Related U.S. Application Data

(60) Provisional application No. 61/771,909, filed on Mar. 3, 2013.

(51) Int. Cl.
| | |
|---|---|
| *B29B 13/02* | (2006.01) |
| *B29C 45/78* | (2006.01) |
| *B29C 45/73* | (2006.01) |
| *F16L 47/02* | (2006.01) |
| *B32B 1/08* | (2006.01) |
| *B29C 57/00* | (2006.01) |
| *B29C 65/18* | (2006.01) |

(52) U.S. Cl.
CPC .............. *B29C 45/78* (2013.01); *B29C 45/73* (2013.01); *B29B 13/024* (2013.01); *B29B 13/025* (2013.01); *B29C 57/00* (2013.01); *B29C 65/18* (2013.01); *B32B 1/08* (2013.01); *F16L 47/02* (2013.01)

(58) Field of Classification Search
None
See application file for complete search history.

(56) References Cited

U.S. PATENT DOCUMENTS

| | | | |
|---|---|---|---|
| 4,661,300 A | 4/1987 | Daugherty | |
| 5,102,324 A | 4/1992 | Bullard et al. | |
| 5,160,396 A | * 11/1992 | Jensen | B29C 33/02 156/304.2 |

(Continued)

OTHER PUBLICATIONS

John Bozzelli, Troubleshooter: How to Solve Uneven Clamping, Apr. 2009, Plastics Technology.*

(Continued)

*Primary Examiner* — Jeffrey Wollschlager
*Assistant Examiner* — Armand Melendez
(74) *Attorney, Agent, or Firm* — John Brooks Law LLC; John J. Brooks, III

(57) ABSTRACT

A moldable material shaping system for shaping a moldable material, the system comprising a thermal transfer mold having an internal cavity configured to receive a moldable material, the internal cavity further comprising an internal mold shape, a thermally controlled heat source subsystem configured to heat the thermal transfer mold and the moldable material received in the thermal transfer mold thereby reshaping the moldable material to a deformed moldable material shape conforming to the internal mold shape. Some embodiments further comprise a cooling source subsystem configured to cool the thermal transfer mold and stabilize the moldable material inside the thermal transfer mold to maintain the deformed moldable material shape. Methods of molding a moldable material are also disclosed.

22 Claims, 18 Drawing Sheets

(56) References Cited

U.S. PATENT DOCUMENTS

| | | | | |
|---|---|---|---|---|
| 5,409,644 | A | * | 4/1995 | Martin ................. A61M 25/001 264/296 |
| 6,048,485 | A | * | 4/2000 | Field .................. A61M 25/001 264/322 |
| 2007/0006441 | A1 | * | 1/2007 | McNiven ................. A61F 2/958 29/508 |
| 2008/0150194 | A1 | | 6/2008 | Thomas |
| 2009/0038756 | A1 | * | 2/2009 | Hongo .................. A61M 39/12 156/303.1 |
| 2009/0218729 | A1 | * | 9/2009 | Pelley ................. A61F 13/2082 264/297.1 |
| 2011/0094653 | A1 | * | 4/2011 | Knapp ................ B29C 65/1412 156/64 |
| 2013/0038053 | A1 | * | 2/2013 | Imanishi ................. B29C 65/14 285/288.1 |

OTHER PUBLICATIONS

PlasticWeld Systems, Tipping and Forming Dies for Catheters and Tubes, Dec. 16, 2010. <http://cathetertipping.plasticweldsystems.com/item/all-categories/tipping-and-forming-dies-for-catheters-and-tubes/item-1015?>.*

* cited by examiner

MOLDABLE MATERIAL SHAPING SYSTEMS AND METHODS OF USE

CROSS-REFERENCE TO RELATED APPLICATIONS

This application claims the benefit of U.S. App. No. 61/771,909, filed on Mar. 3, 2013, entitled "MOLDABLE MATERIAL SHAPING SYSTEMS AND METHODS OF USE," the entire contents of which are incorporated herein by reference.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

1. Field of the Invention

This invention relates to systems and methods to shape moldable materials, in particular systems and methods of deforming moldable materials utilizing a stably and uniformly controlled heating source.

2. Description of the Prior Art

Tubes such as catheters are commonly made from moldable materials such as plastic extrusions. Various thermal processing methods known in the art are employed to fabricate the tubes into functional products such as catheters for their intended use. Processes typically performed are tipping, joining, flaring, necking, sinking, laminating and forming. These processes typically incorporate heating the plastic to soften these materials so they can be reformed into another configuration that is retained when the material is cooled. These processes typically require the use of molds or dies during the reshaping of the material. One of the common processes in catheter manufacturing is producing a tip at the distal end of the catheter body. A tip is end rounded or tapered from a larger diameter down to a smaller diameter to allow for atraumatic introduction into the patient. Catheter tips may also be reformed so as to conform to accessory devices such as guidewires, needles, dilators or introducers. In order to produce an acceptable tip, various means have been introduced over recent history where a mold is made of different materials or methods such as stainless steel, electroformed molds, glass or other high temperature materials such as polytetrafluoroethylene. These molds are heated by different methods such as mounting them in a heated block, using a hot air gun to heat it or using radio frequency (RF) energy to heat the mold in the case of metallic molds containing iron.

One example of a system is detailed in U.S. Pat. No. 5,102,324 filed Jan. 22, 1990 of Worldwide Medical and entitled Precision Tipping Device for Surgical Catheters, which is herein incorporated by reference in its entirety, where a mold with the desired configuration is mounted onto a heated block. The heated block transfers the heat to the mold by conduction while the block is maintained at the desired temperature. The material to be tipped is clamped by a gripper and advanced into the mold by a programmable slide powered by a stepper motor. Once the material enters the mold, it is melted or softened by the heat conducted through the mold allowing reshaping of the plastic to the shape of the mold. Once heated and reshaped the material must be cooled below the softening temperature to freeze the plastic into the new shape and allow for removal from the mold. In this example, a stream of air is directed at the mold for a period of time determined by the operator. After the appropriate time, the slide returns to a home position after the cooling cycle and is ready to repeat the cycle.

Another method as shown in U.S. Pat. No. 4,661,300 filed Mar. 11, 1986 by Becton, Dickinson and Company entitled Method and Apparatus for flashless tipping of an I.V. Catheter, which is herein incorporated by reference in its entirety, details a system using a radio-frequency (RF) energy source to heat a specially designed mold with cooling channels integrated into the mold assembly to facilitate the cooling process after the heat forming sequence. This process also includes a programmable slide and other required programmable process conditions.

U.S. Pat. No. 6,048,485, filed Dec. 13, 1996 entitled "Thermal Gradient Beveling of Catheters" by Johnson and Johnson, which is herein incorporated by reference in its entirety, details an attempt to address one of the major issues of forming catheter tips. This relates to confining the appropriate heated section of the mold to the tip area to be formed. It is desirable to prevent the heat from migrating along the length of the tipping mold towards the body of the catheter resulting in heating an area of the catheter that does not require reforming producing a poor result. U.S. Pat. No. 6,048,485 details a tipping mold with a high heat and a low heat zone separated by an insulated material such as ceramic or Titanium. Operationally, the mold is in fixed contact with a heated block and as the catheter material is advanced into the mold, it melts or is softened by the heat and flows into the cavity. Once it has reached the travel limit set by the controls a blast of air cools the mold and formed catheter tip. Once cooled, the catheter is removed and a new cycle can be started. The insulator helps to prevent the high heat zone of the mold from traveling away from the tip towards the body of the catheter preventing overheating in the body area.

Patent Application Publication US 2008/0150194 corresponding to U.S. patent application Ser. No. 12/003,002, filed Dec. 19, 2007 and entitled Apparatus and Methods of End Forming Tubes, which is herein incorporated by reference in its entirety, describes a system utilizing glass molds with a detailed inside shape conforming to a particular tip design. The glass mold is mounted onto a heated block to provide the heat to form the tip and once formed, the glass mold is cooled by an air blast and the part is removed.

There are numerous commercially available catheter tipping machines on the market fundamentally using RF for the heating process. A few known companies are Plastic Weld, Vante and Cath-Tip.

All of the U.S. Patents and U.S. Patent Applications referenced above and elsewhere in this application are herein incorporated by reference in their entirety.

BRIEF SUMMARY OF THE INVENTION

The following summary is included only to introduce some concepts discussed in the Detailed Description below. This summary is not comprehensive and is not intended to delineate the scope of protectable subject matter, which is set forth by this description and the claims presented at the end.

In one example embodiment of a moldable material shaping system, the system may address and mitigate the limitations of previous methods of forming a moldable material, such as a catheter tip, with methods and subsystems that more accurately control the flow, stability and/or uniformity of heat, prevent overheating, reduce heating and cooling times and to isolate the processing zone only to the area of interest. In some embodiments, the speed, accuracy, yield and repeatability of the process to shape a moldable material is improved.

In one example embodiment, a moldable material shaping system for shaping a moldable material, such as a plastic tube, is provided, said system comprising a thermal transfer mold having an internal cavity configured to receive a moldable material, the internal cavity further comprising an internal mold shape, a heat source subsystem configured to heat a portion of the thermal transfer mold and the moldable material received in the thermal transfer mold thereby reshaping the moldable material to a deformed moldable material shape conforming to the internal mold shape. Some embodiments further comprise a cooling source subsystem configured to cool the thermal transfer mold and stabilize the moldable material inside the thermal transfer mold to maintain the deformed moldable material shape.

In some embodiments, the thermal transfer mold comprises a thin wall mold made from a heat conductive material whereby the thin wall mold can rapidly transfer heat and cold. In some embodiments, the thin wall mold further comprises a wall having a wall thickness within a range between 0.065 inches and 0.004 inches. In some embodiments, the thin wall mold further comprises a wall having a wall thickness within a range between 0.014 inches and 0.008 inches. In some embodiments, the thin wall mold further comprises a closed distal end. In some embodiments, a distal end of the thin wall mold further comprises a mandrel coupled to an interior mold shape configured to fit into a distal lumen of the moldable material. In some embodiments, a distal end of the thin wall mold further comprises a through hole configured to receive a mandrel. In some embodiments, the heat source subsystem comprises a convective heat source and in some embodiments the heat source subsystem comprises a conductive heat source.

In some embodiments, the heat source subsystem is configured to mate with a portion of the thermal transfer mold whereby the heat source can uniformly heat the portion of the thermal transfer mold and the moldable material within the thermal transfer mold. In some embodiments, the heat source subsystem is configured to stably control the heating of the portion of the thermal transfer mold within a temperature range of less than 20 degrees Fahrenheit for a temperature time period of greater than one half of a second and the heat source subsystem is configured to uniformly control the heating of the portion of the thermal transfer mold within a temperature uniformity range such that a temperature at one point of the thermal transfer mold is no greater than 30% from a temperature of all other points of the thermal transfer mold. In some embodiments, the heat source subsystem is configured to stably control the heating of the portion of the thermal transfer mold within a temperature range of less than 2 degrees Fahrenheit for a temperature time period of greater than 2 seconds and the heat source subsystem is configured to uniformly control the heating of the portion of the thermal transfer mold within a temperature uniformity range such that the temperature at one point of the thermal transfer mold is no greater than 10% from a temperature of all other points of the thermal transfer mold.

In some embodiments, the heat source subsystem comprises a heat core configured to transfer heat to the thermal transfer mold and the heat core is positional/movable relative to the thermal transfer mold whereby the core may be moved to not transfer heat to the thermal transfer mold. In some embodiments, the heat core is interchangeable with a second heat core and the heat core and the second heat core are configured to mate with an external portion of the thermal transfer mold.

In some embodiments, the moldable material shaping system further comprises a mold clamp removably securing a proximal end of the thermal transfer mold to the mold clamp and an insulation layer positioned between the proximal end of the thermal transfer mold and the mold clamp whereby the heat flow from the thermal transfer to the mold clamp is reduced.

In some embodiments, the cooling source subsystem provides a cooling source comprised of one selected from a group consisting of compressed air, water, cooling fins and heat exchanger coils.

In some embodiments, the cooling source subsystem provides a cooling source comprised of a moveable split heat sink element configured to be clamped around the thermal transfer mold.

In some embodiments, the cooling source subsystem is configured to stably control the cooling of the portion of the thermal transfer mold within a temperature range of less than 20 degrees Fahrenheit for a temperature time period greater than one half of a second and the cooling source subsystem is configured to uniformly control the cooling of the portion of the thermal transfer mold within a temperature uniformity range such that a temperature at one point of the thermal transfer mold is no greater than 30% from the temperature of all other points of the thermal transfer mold.

In some embodiments, a moldable material shaping system for shaping a plastic tube is provided comprising a thermal transfer mold having an internal cavity with a first open end and a second open end, the internal bore sized to receive a portion of a first moldable material in the first open end and a portion of a second moldable material in the second open end, a heat source subsystem having a heat chamber sized to receive and heat a portion of the thermal transfer mold and the portions of the first and second moldable materials received in the thermal transfer mold, the heat source subsystem comprising two or more positional heat cores, the positional heat cores are positional between a heating position and a cooling position whereby the heating position places the heat chamber in a proximity of the thermal transfer mold whereby the heat chamber heats the portion of the thermal transfer mold and the cooling position places the heat chamber away from the thermal transfer mold whereby the thermal transfer mold is cooled and a control subsystem configured to control the heat source subsystem whereby the portions of the first and second moldable materials are joined.

In some example embodiments, a moldable material shaping method is provided, the method comprising rapidly heating a thermal transfer mold with a heat source, deforming a moldable material received in the thermal transfer mold to a deformed moldable material shape conforming to an internal mold shape of the thermal transfer mold, removing the heat source from the thermal transfer mold and stabilizing the deformed moldable material shape.

Other advantages and features of embodiments of the systems and methods disclosed will be apparent from the following description of embodiments and from the claims.

BRIEF DESCRIPTION OF THE SEVERAL VIEWS OF THE DRAWINGS

In order that the manner in which the above stated and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Figure 1:
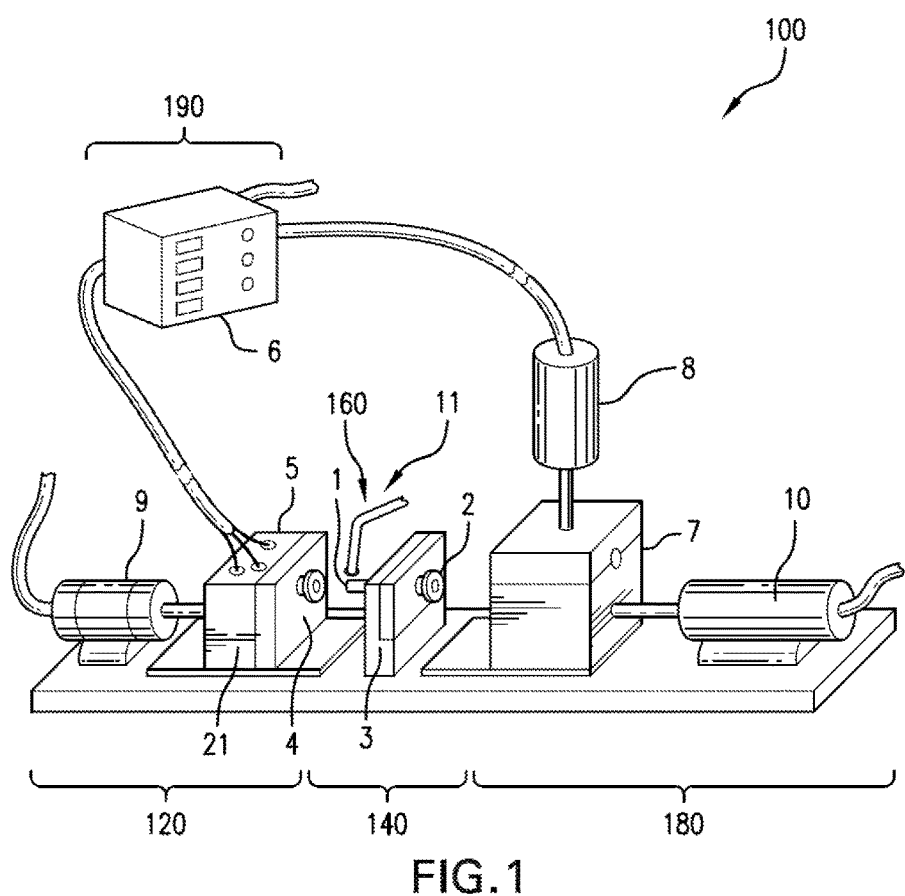
FIG. 1 is a perspective illustration of one example embodiment of the moldable material shaping system.

Disclosed are moldable material shaping systems and methods capable of shaping tubes for applications such as, but not limited to tipping, joining, flaring, necking, sinking, laminating or forming catheters. In general, embodiments of the moldable material shaping systems and methods provide systems and methods to stably and uniformly control the application of heat onto a moldable material contained in a mold subsystem by controlling the relationship between the mold subsystem or die and a heat source subsystem and controlling the heat source subsystem. The relationship of the mold subsystem and the heat source subsystem may be determined by controlling their relative positioning using a control subsystem. The control of the heat source subsystem may limit the time heat is applied to the mold subassembly by quickly removing the heat source subsystem from the mold subsystem. The control of the heat source subsystem may also provide a means to prevent overheating of the mold subsystem thereby preventing material degradation, material discoloration and mold damage by using thermocouples or sensors such as non-contact sensors. The sensors allow for stable thermal control of the heat source subsystem and allow for temperature monitoring during the heating of the mold subsystem. Configuration and design of the heat source subsystem and its components may also provide uniform control of heating and cooling of the thermal transfer mold.

Adjustments to the relative positioning between the mold subsystem, comprising a thermal transfer mold, and heat source subsystems may be determined by using the heat transfer formula supplied herein and the heat transferred to the wall of the thermal transfer mold and from the thermal transfer mold wall to the plastic moldable material through convection or conduction. The heat transfer calculation is identified by the formula below:

$$\frac{Q}{t} = \frac{\kappa A(T_{hot} - T_{cold})}{d}$$

Active formula: Heat conduction $Q$/Time=(Thermal conductivity)×(Area)×$(T_{hot}-T_{cold})$/Thickness The heat transfer per unit surface through convection and the relation is known as the Newton's Law of Cooling.

The equation for convection can be expressed as:

$$q = h_c A dT$$

where q=heat transferred per unit time (W)

A=heat transfer area of the surface (m°)

$h_c$=convective heat transfer coefficient of the process (W/m$^2$K or W/m$^{2\circ}$ C.)

dT=temperature difference between the surface and the bulk fluid (K or ° C.)

In some embodiments, the systems and methods utilize thin wall mold technology in the mold subsystem and thermal transfer mold. In some embodiments, the thin wall mold technology provides for rapid heat transfer through the thin wall mold thereby enabling the melting and reshaping of a moldable component, such as a plastic catheter into another desired shape and subsequently rapidly cooling of the moldable component into the new shape upon removal of the heat source and rapid cooling of the thin wall mold.

The moldable material shaping systems may be used to shape a wide variety of plastic materials. As used throughout this description, plastic includes any of a group of synthetic or natural organic materials that may be shaped when soft and then hardened, including many types of resins, resinoids, polymers, cellulose derivatives, casein materials, and proteins. Plastics may also be known by trademark names such as but not limited to Alathon, Estane, Pebax, Pellethane, Teflon and many more thermoplastic as identified by the Society of Plastics Encyclopedia. Particularly suitable plastic materials for catheters include, but are not limited to, nylons, polyether block amide's, polyethylene's, polyurethane's, vinyl's and polytetrafluoroethylene's.

One Embodiment of the Moldable Material Shaping System:

Referring now to the example embodiment in FIG. 1, there is shown an example moldable material shaping system 100 having a heat source subsystem 120 and a mold subsystem 140, the mold subsystem comprising a thermal transfer mold having an internal mold shape configured to receive a moldable material. The heat source subsystem is generally configured to heat the thermal transfer mold and the moldable material received in the thermal transfer mold thereby reshaping the moldable material to a deformed moldable material shape conforming to the internal mold shape. As shown, the moldable material shaping system 100 may also comprise a cooling source subsystem 160, a gripping subsystem 180 and a control subsystem 190. The cooling source subsystem 160 is generally configured to cool the thermal transfer mold and stabilize the moldable material inside the thermal transfer mold to maintain the deformed moldable material shape. The cooling source subsystem 160 may cool the moldable material while inside the thermal transfer mold.

The heat source subsystem 120 is configured to heat the thermal transfer mold and the moldable material received in the thermal transfer mold thereby allowing the moldable material to be reshaped to a deformed shape conforming to the internal mold shape. The heat source subsystem 120 may comprise a heat source or heating elements designed to maintain a temperature needed to deform the moldable material. In the embodiment shown, the heat source is a heat core 4. The heat source subsystem 120 may also comprise additional elements such as an activating motor 9, a heat block assembly 5 that may be positionable by a slide mechanism 21 and connections to the control subsystem 190. The heat source subsystem 120 may be used as a conductive or a convective heat source.

Figure 15:
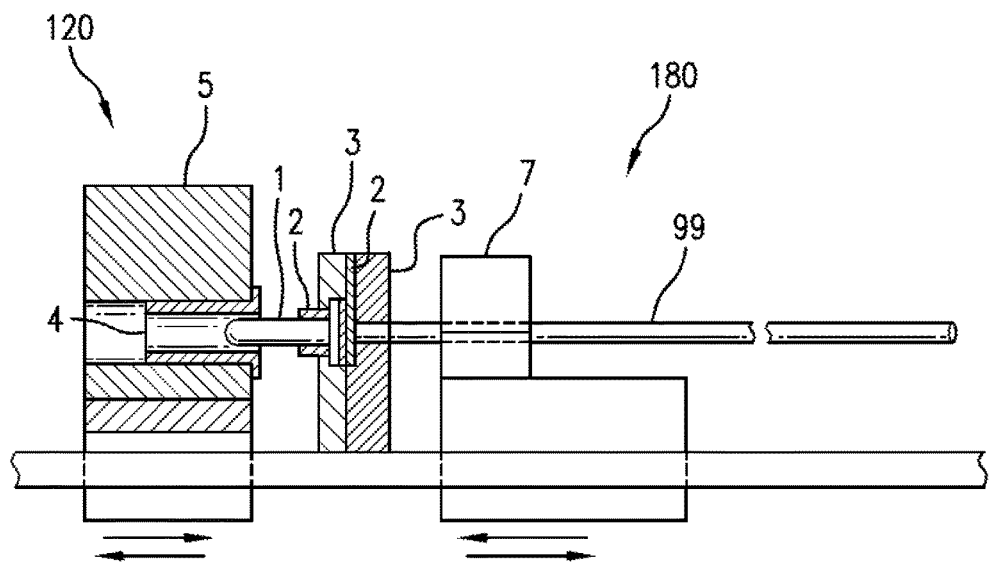
FIG. 15 illustrates one embodiment of a heat block assembly, a mold subsystem and a sliding gripper.

The mold subsystem 140 generally comprises a thermal transfer mold 1 to transfer heat and cold to an internal cavity of the thermal transfer mold 1. The thermal transfer molds are purposely designed to allow heat transfer uniformly from the heat source subsystem 120. In some embodiments, the thermal transfer mold 1 comprises a heat conductive material such as a thin metal material that allows for rapid heat transfer such as nickel, aluminum, stainless steel or brass. In the embodiment shown in FIG. 2A, the mold subsystem 140 comprises the thermal transfer mold 1, a mold holder 2 and a mold clamp 3. The mold holder 2 secures and holds the thermal transfer mold 1 so that it can be positioned to align with the heat core 4 that is attached to the heat block assembly 5. The mold holder 2 may be comprised of a insulating material. The mold clamp 3 comprises a design to clamp and hold the mold holder 2 and the thermal transfer mold 1 in position for molding the moldable material. The mold holder 2 may utilize a insulated material to insulate the thermal transfer mold 1 from the mold clamp 3 thereby limiting the heat required for the forming process to be conducted away from the mold. As shown in FIG. 15, the insulated mold holder 2 secures the thermal transfer mold 1 to the mold clamp 3 and when the mold clamp is secured to a base, the heat source subsystem 120 and the gripping subsystem 180 position the heat source and the moldable material properly with respect to the thermal transfer mold.

Referring back to FIG. 1, the thickness of the thermal transfer mold wall may be any thickness that allows for efficient heat transfer. In some embodiments, the thermal transfer mold may comprise a thin wall mold or die with a wall thickness that may range from 0.004 inches to as thick as 0.065 inches. In some embodiments, the preferred wall thickness may also range from 0.006 inches to 0.018 inches, or 0.008 inches to 0.016 inches or 0.008 inches to 0.014 inches or 0.008 inches to 0.012 inches or preferably 0.008 inches to 0.010 inches. This wall thickness may be determined by the size of the moldable material, the knowledge from the characteristics of the wall material (from the supplier's specification) and the heat transfer calculation as identified above. The interior cavity of the thermal transfer mold is defined by interior walls of the thermal transfer mold. The interior cavity is configured to receive a portion of a moldable material and has an interior mold shape. A first, proximal end of the interior cavity allows the moldable material to be received and the other end of the interior cavity has an interior mold shape defining a tip shape for the tip of the moldable material. The other end, the distal end of the thermal transfer mold may be a closed distal end.

The design of the thermal transfer mold may be produced by electroforming, stamping or machining. Thin wall thermal transfer molds allow for rapid heat transfer to the targeted temperature due to a lower mold mass than thicker machined metal molds, cast metal or glass molds. The electroformed nickel process allows for repeatable mold fabrication. The material composition used in the making of the mold is not as critical as the materials used to make molds used in the RF induction machines which require a certain type of metal. Suitable materials for thin wall molds in the present systems include, but are not limited to, electroformed nickel or stainless steel.

Referring again to FIG. 1, the cooling source subsystem 160 is generally configured to provide a cooling source to cool the mold subsystem and stabilize the moldable material inside the mold subsystem to maintain the deformed shape. The cooling source subsystem may generally be comprised of a nozzle 11 that is positioned to direct a coolant, such as air, to cool the thermal transfer mold after the shaping. The cooling source subsystem may be designed to use air, water, compressed air or any other coolant as the cooling source. The cooling source subsystem may also be designed to use cooling fins, heat sinks or heat exchanger coils to function as the cooling source. The cooling source subsystem may also further comprise a coolant storage system and a pump to transfer the coolant from the storage system to the nozzle. The cooling source subsystem may also be operably coupled to the control subsystem. In some embodiments, the cooling source is a moveable or positionable split heat sink configured to be clamped or positioned around the thermal transfer mold.

Figure 2A:
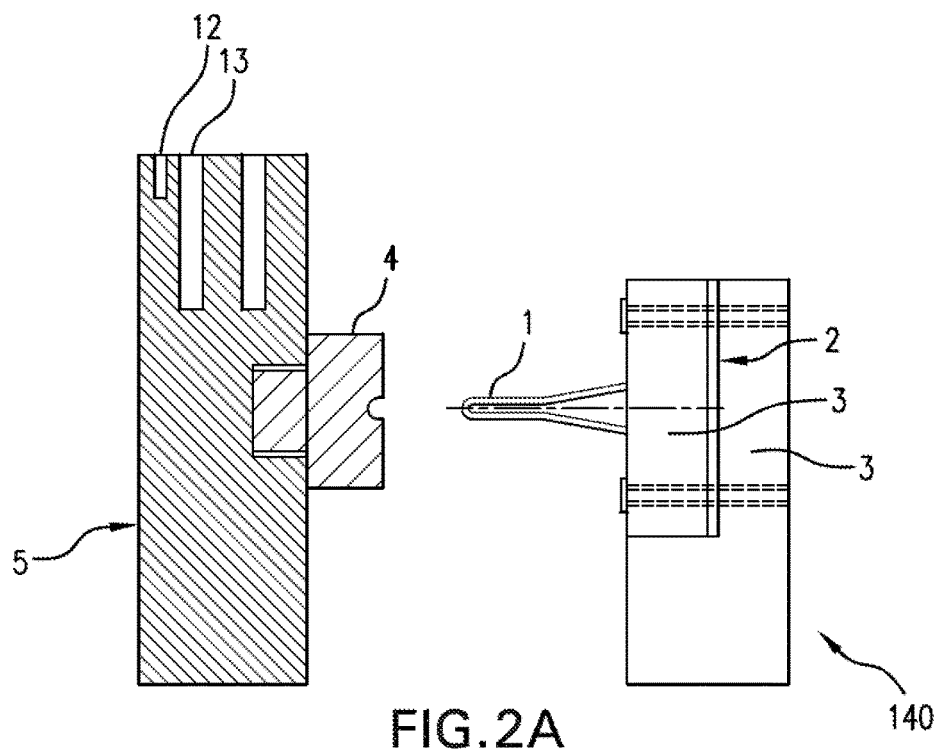
FIGS. 2A-2C illustrate example components of one embodiment of the moldable material shaping system in a sequence of use to tip a catheter.

The gripping subsystem 180 generally secures the material to be molded and aligns the mold subsystem with the heat source subsystem. In one embodiment, the gripping subsystem comprises a linear slidably positional assembly that is positioned in line with the mold and a controlled travel distance and provides an even pushing pressure to the moldable component so that it fills the thermal transfer mold. As shown in FIG. 2A, the tip of the thermal transfer mold 1 may be aligned with a matching or mating heat core 4 which is received in a temperature controlled heat block assembly 5 whose function is controlled. As shown in FIG. 15, a sliding gripper subsystem 180 designed to hold moldable extrusion components 99, such as plastic, is aligned with mold 1 and heat core 4 where the part to be molded is placed into mold 1 and gripper 7 and securely gripped by activating a screw or cam, a motor or air cylinder (not shown). This motor (not shown) urges the moldable component 99 and the gripper 7 towards and away from the mold subassembly 140. Maintaining consistent pressure onto the moldable component 99 using controlled pressure allows the moldable component 99 to reshape into a deformed shape conforming to interior mold shape while the moldable component 99 is moldable. The gripping subsystem 180 provides even pushing pressure to urge the moldable component 99 to fill the mold 1 and may also provide a controlled speed for moving system components.

The control subsystem 190 as shown in FIG. 1 generally provides a means to control the heating and cooling of system components and program the timing and cycle sequencing via basic machine inputs using either a programmable logic controller or air valve logic. In some embodiments, the control subsystem comprises a control box 6 operably coupled to systems element such as the heat source subsystem 120 and the gripping subsystem 180. The control subsystem 190 may provide a range of adjustments and controls to process many different sizes of catheters as well as many different types of moldable components and materials. This system may be controlled by using a human machine interface (HMI) through a computer process unit. In some embodiments, the control subsystem uses technologies known in the art for mechanical temperature control systems and incorporates the use of a programmable logic controller (PLC) with human machine interface (HMI) capabilities. The shaping methods, in using a stable temperature controlled by the PLC, offers the operator a specific period of time to shape the component without the temperature over shooting to a higher temperature to cause the moldable component to overheat and degrade. The stable temperature may be maintained within a suitable temperature range and at a recommended temperature recommended by the moldable material suppliers. The control subsystem 190 helps provide well controlled, stable and rapid localized heating and cooling to the thermal transfer mold 1 for the purpose of shaping portions of the material, shaping tips, joining the thermoplastic tubes together end to end, necking down a tube or rod to a smaller diameter, sinking braided reinforcements in tubing or laminating two or more tubes or materials together.

Figure 3A:
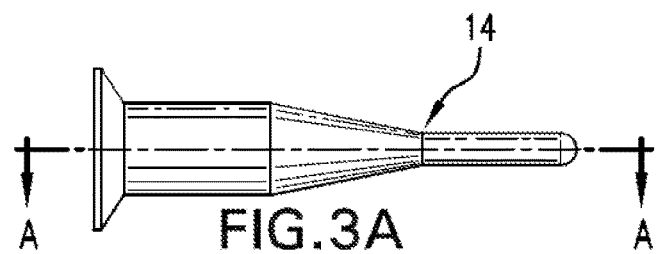
FIGS. 3A-3E illustrate example embodiments of open end and closed end thin wall tipping molds.
Figure 3B:
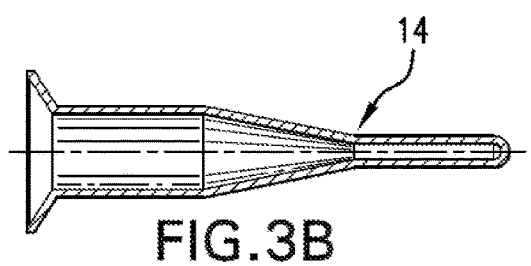
Figure 3C:
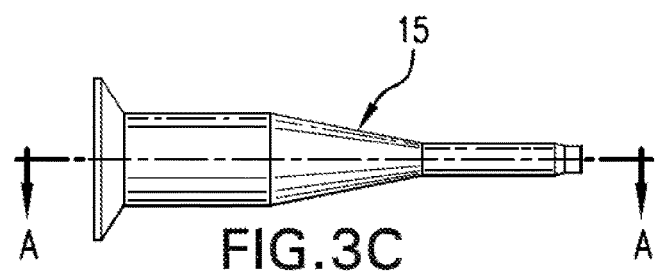
Figure 3D:
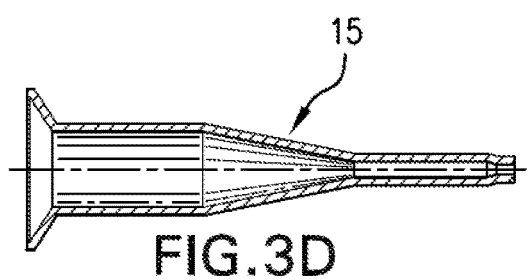
Figure 3E:
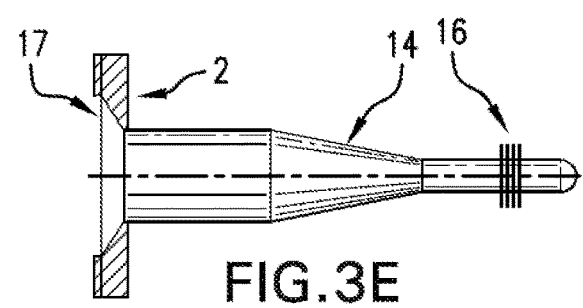

Alternative embodiments of the thermal transfer mold are illustrated in FIGS. 3A-3E. FIG. 3A depicts one example embodiment of a closed end thin wall mold 14 for applications such as tipping closed end catheters or plastic guidewire blunt tips. FIG. 3B depicts a cross sectional view of closed end mold 14. FIG. 3C depicts one example embodiment of an open end thin wall mold 15 for applications such as tipping catheters requiring a thru hole formed into the catheter tip. With this embodiment, a removable mandrel (not shown) is configured to fit into the distal end of the catheter and prevents the distal end from forming a closed end during the forming process. In some embodiments with a mandrel, the mandrel may be coupled to the interior mold shape and be configured to fit into the distal lumen of the moldable material. FIG. 3D depicts a cross sectional view of the open end mold 15 of FIG. 3C. FIG. 3E depicts one example of a thermal transfer mold with cooling fins 16 present on the outside of the mold 14 which are used to rapidly remove heat during cooling or to function as a heat dam during a heating cycle. The cooling fins are designed to act like a heat-sink component drawing heat away from the mold as the fins are cooled and may also allow for maintaining a heat temperature in the specified area for a length of time if the fins are not cooled. FIG. 3E also shows the mold holder 2 comprising insulating material around the large open end 17 of the thermal transfer mold. This insulation layer (mold holder 2) is positioned between the proximal end of the thermal transfer mold and the mold clamp to insulate the thermal transfer mold 14 from conducting heat from thermal transfer mold tip to the stationary mold clamp (not shown) when thermal transfer mold 14 is securely attached to mold clamp 3 in FIG. 1. This insulation reduces the heat flow from the thermal transfer mold to the mold clamp and assists the heat source subsystem to maintain a uniform and stable temperature. As shown in FIGS. 3E and 15, the insulation layer may be positioned on both sides of the proximal end of the thermal transfer mold, such as the widened flange of the open end 17, to reduce the heat flow from the thermal transfer mold. In some embodiments, the thermal transfer mold has a through hole through its distal end for a mandrel that will be positioned in the lumen of a catheter extrusion and passed through the thermal transfer mold during the heating cycle.

Figure 4:
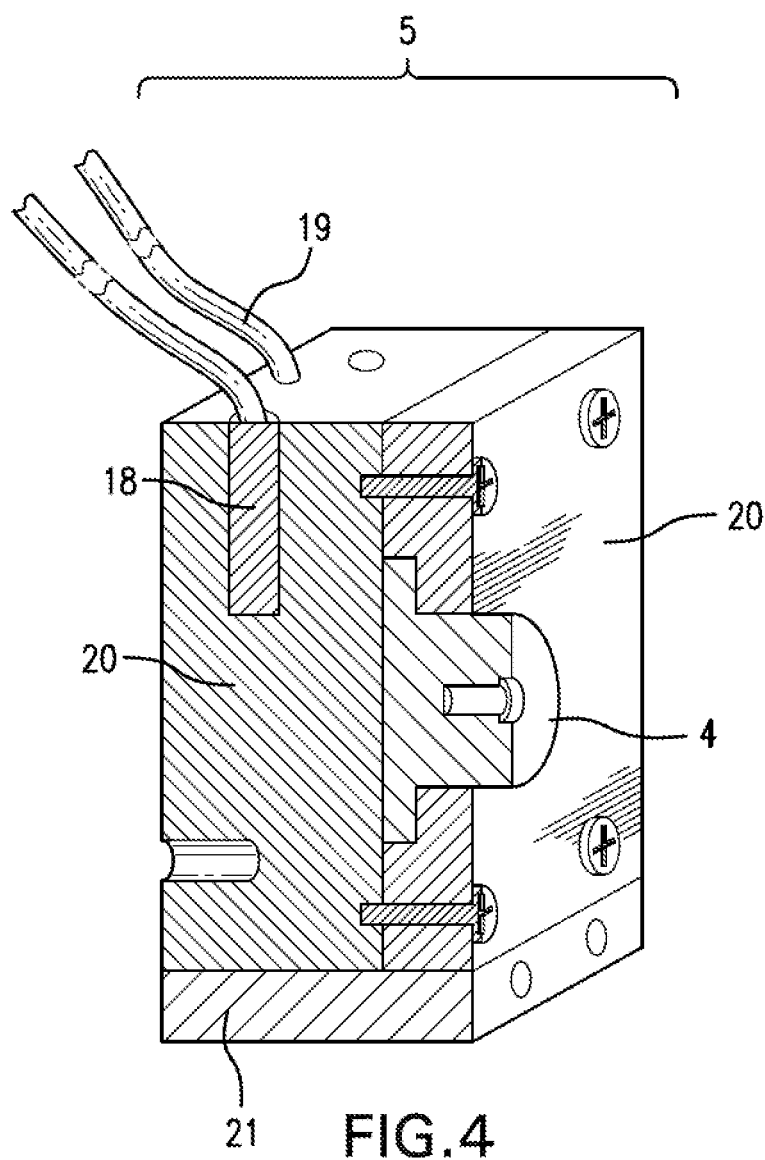
FIG. 4 illustrates a cross sectional view of one embodiment of a slidable heat block assembly comprising a heat block assembly mounted onto a thermal insulation component comprised of a heating element with thermocouple and interchangeable heat core.

One example embodiment of the heat block assembly 5 of the heat source subsystem is shown in FIG. 4. FIG. 4, illustrates a cross-section of one possible configuration of a heat block assembly comprising a slidably positional heat block assembly 5 comprised of a heat block 20, a interchangeable heat core 4, a heating element 18 with thermocouple 19 connected to a control box 6 (shown in FIG. 1). The heating element may be a resistance heating element. The heat block assembly 5 may have its positioning and alignment controlled by attachment to an activating motor 9 (shown in FIG. 1) and slide mechanism 21 such as a lead screw driven slide or a pneumatic driven slide. The heat block 20 is designed to receive and secure the heat core 4 and allow for easy interchange of heat cores when needed. The heat block 20 is also configured to transfer heat from the heating element 18 to the heat core 4. The heating element 18 is controlled by the temperature controller in the PLC and the temperature is monitored by a thermocouple 19. Although FIG. 4 shows that the heating element 18 is perpendicular to the bore of the heat core, it is understood that the heating element 18 may comprise multiple heating elements and the heating elements may be configured differently to better transfer and control the temperature of the heat block and/or the heat core. For example, multiple heating elements may be placed evenly around a circular heat core to stably and uniformly control the temperature of all portions of the heat core. To keep the heat from transferring to other places other than the heat block assembly a layer of heat insulator may be used to reduce heat migration. The heat source subsystem may be covered with a screen to prevent the operators from being burned. In some embodiments, the heat block assembly may be suspended from an assembly bottom by a u-channel and fan that allows the heat block assembly to be cooled. In some embodiment, the heat block assembly is open to the air to help dissipate the heat. The heat block 20 and the heat core 4 may be made from any material that is able to transfer heat. Suitable materials for the heat core 4 and the heat block 20 include but are not limited to aluminum, brass and stainless steel.

The heat source subsystem has a mating portion specifically shaped to receive a portion of the thermal transfer mold. Generally, the mating portion is part of the heat core and conforms to the tip portion of the thermal transfer mold external shape that is to be heated and includes those portions/areas of the heat core configured to transfer heat to the heat transfer mold.

Figure 6A:
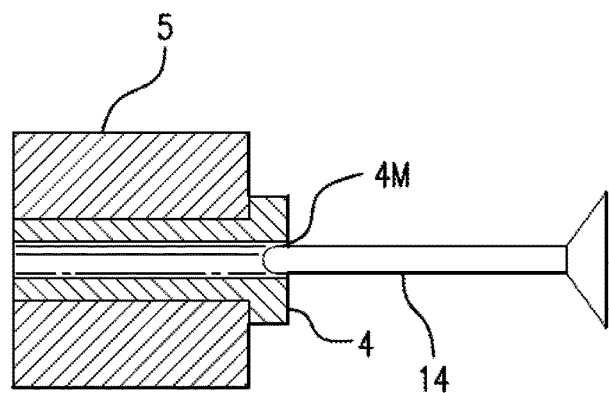
FIGS. 6A-6C illustrate embodiments of convection and conduction heating configurations with a heat core assembly.

FIG. 6A illustrates a cross section of one embodiment of the heat core 4 within a heat block 5 wherein the heat core 4 utilizes convection to heat the tip portion of the thermal transfer mold 14. In this embodiment, the mating portion 4M of the heat core 4 is in close proximity of the thermal transfer mold 14 but not in contact with it thereby providing for precise positioning and adjustment to control the heating area of the thermal transfer mold. In one embodiment, the mating portion of the heat core is an extended bore through the heat core and the tip portion of the thermal transfer mold has an external shape uniformly occupying space in the bore but not in contact with the heat core. It is understood that any sized gap may be provided so that sufficient heat transfer is provided as required for the methods disclosed. The gap size will depend on the mold shape and the material to be molded. Typically, but not for limitation, a gap of less than 35% of the diameter, width or height of the bore or mating portion of the heat core would be a sufficient gap. For these example embodiments, a gap of about 0.010 to 0.030 inches between the outer surface of the thermal transfer mold and the interior surface of the heat core bore provides sufficient room for positioning the thermal transfer mold while also allowing sufficient heat transfer from the heat core.

Figure 6B:
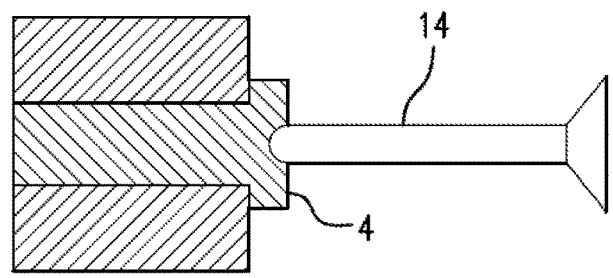
Figure 6C:
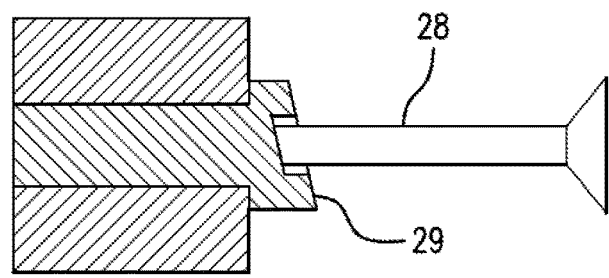

FIG. 6B shows one embodiment of the heat core 4 utilizing conductive heating of the thermal conductive mold 14 by heat core 4 as a conductive heat source. In this embodiment, the direct contact or mating between the mold 14 and mating portion of the heat core 4 may provide for faster transfer of heat between mold 14 and heat core 4 than the convective heating depicted in FIG. 6A. FIG. 6C shows an alternative configuration of conductive heating of the beveled mold 28 by directly contacting a machined angled of beveled mating cavity in heat core 29 providing for a uniform heat zone depth uniformly around beveled mold 28. In one embodiment, the mating portion of the heat core is a concave recess and the tip portion of the thermal transfer mold external shape is a convex protrusion shaped to mate in the concave recess of the mating portion of the heat core shape. This mating allows for a controlled area of heat transfer to that portion of the heat transfer mold and only softens and melts the area of concern of the moldable material while other sections or areas of the moldable material are not softened or melted. This mating portion can be designed to have any dimension of depth or width of the concave recess to mirror and mate with any dimension of length or width of the convex protrusion of the tip portion of the thermal transfer mold.

Figure 13A:
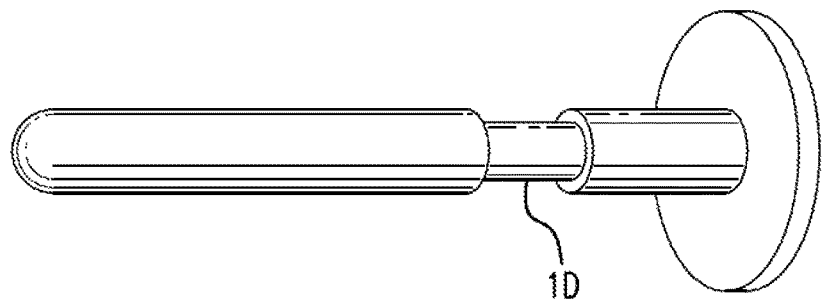
FIG. 13A illustrates an example thermal transfer mold with one embodiment of a heat dam.
Figure 13B:
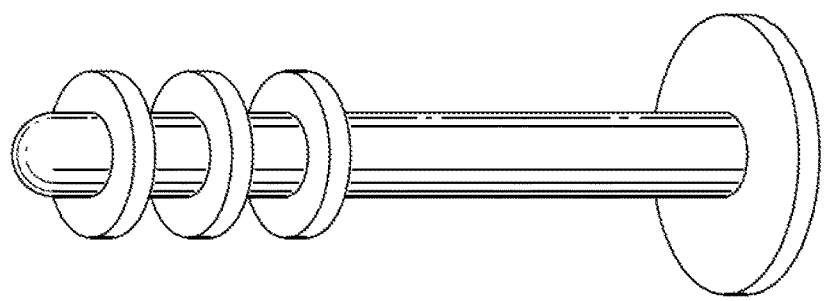
FIG. 13B illustrates an example thermal transfer mold with one embodiment of a heat sink.

Some embodiments may also provide a heat dam used for either heating or cooling. As shown in FIG. 13A, the heat dam is a change in the mass or dimension of the thermal transfer mold that functions as a temperature restrictor creating a heat differential between where the heat source applies heat to the thermal transfer mold and other portion of the mold where heat is not desired. In some embodiments, the heat dam is a machined area 1D on the heat transfer mold where the thickness is reduced to restrict the heat from conductive heat transfer or keep the heat from migrating too quickly away from the area of concern. FIG. 13B shows cooling fins to prevent heat from migrating from the tip area to the moldable material body area.

Figure 5:
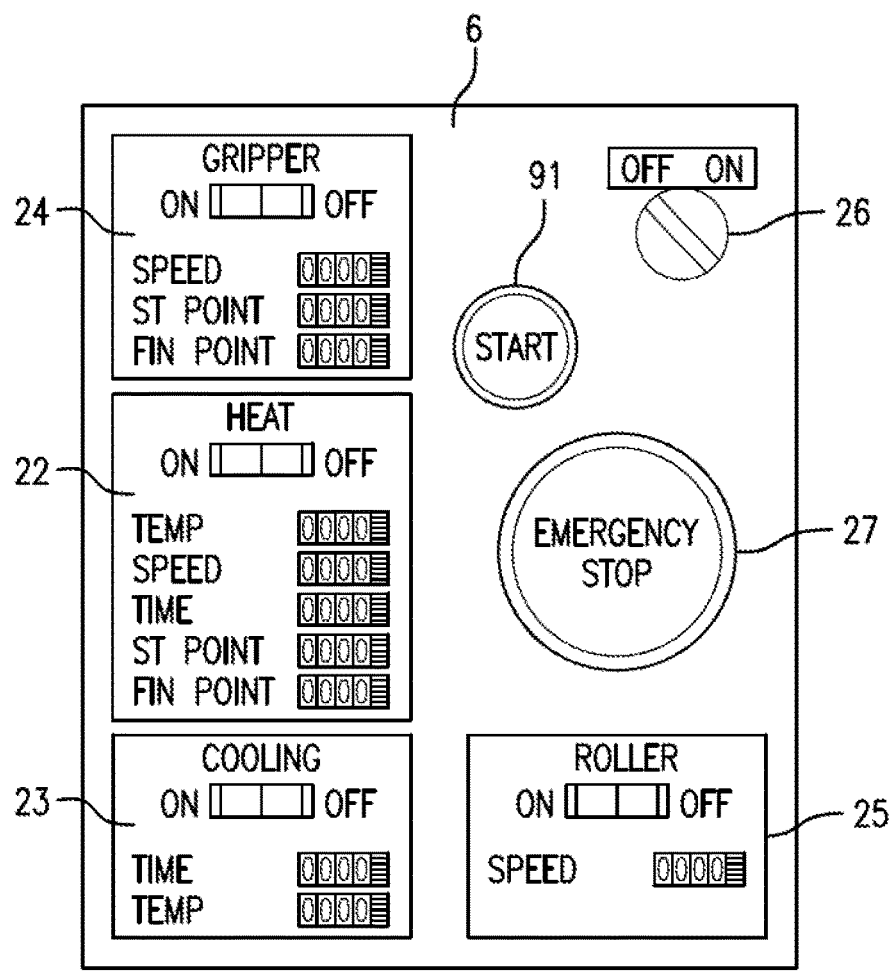
FIG. 5 illustrates one embodiment of the control box configured with a programmable logic controller (PLC) and using pneumatic control switching mechanisms.

One example embodiment of the control subsystem is shown in FIG. 5. illustrating a control subsystem comprising a control box 6 to manage the moldable material shaping system heating 22 and cooling 23 functions of the thermal transfer mold, gripper controller 24 for gripping plastic component to be molded, roller controller 25 when used for necking, sinking or laminating and power on/off 26 and emergency stop 27. FIG. 5 also illustrates an example embodiment of a control box 6 using an internal PLC. The on/off switch 26 turns the unit on or off and gripping controller 24 with push/pull controls the gripper and the speed of the moldable material when advanced into the mold. The heat controller 22 allows for adjustment of the heat in the heat block assembly subsystem and it monitors and maintains the temperature with the use of a thermocouple. The motor controller 25 allows for the gripper and draw speed needed for necking, sandwiching and draw down assembly (not shown). The cooling controller/timer 23 allows for air or fluid spray to cool the tipping molds. The emergency stop 27 is a safety switch to stop all processes and re-set the unit. The start button 91 initiates the thermal forming cycle.

The control subsystem may also provide a means to prevent overheating of the thermal transfer mold by using thermocouples or non-contact sensors thereby preventing material degradation, material discoloration and mold damage. The thermocouples or sensors allow for stable heat control and allow for temperature monitoring during the heating and cooling processes. The PLC controller sensors are part of the PLC controller which is well known in the industry for heat and motor control movement. The mechanical stops not shown are used for accurate positioning of the heat block assembly and the gripper assembly. The mechanical stops prevent excess pressure from being applied to the moldable material during the tipping process which can cause the material to buckle.

In some embodiments, the heat source subsystem is capable of providing a stable heat source through the use of the PLC with HMI capabilities. The output temperature is maintained by a thermocouple attached to the heat source subsystem. This thermocouple is used as a temperature sensor to monitor and control when the PLC turns on or off the heat element to control the temperature of the heat source subsystem. The thermocouple is attached directly to the heating subsystem and gives constant temperature monitoring to the moldable material shaping system. In addition, the thermocouple controls the temperature transferred to the heat core for the transfer of heat from the heat core to the thermal transfer mold. The thermocouple will also allow the user to set a predetermined temperature on the PLC to monitor and control the heat core temperature within a temperature range as described below.

The disclosed heat source subsystem is different than systems that utilize an RF generator and associated controls as the heat source and can be less expensive and less complex. The RF generator generates the heating energy by a combination of a wrapped copper coil and a mold positioned inside the coil. The shape and material of the RF activated mold has to be carefully matched to the distance and position of the RF coils and the inside circumference of the wrapped RF coil; it is wound with multiple wraps and shaped to surround the mold. The coil positioning in relationship to the tipping mold is critical to a repeatable process when reconfigured by catheter set-up operators. The original size and positioning of the coil is usually set by the sellers of the induction machine at the time of purchase and it's known to the induction heating industry that the closer the coils are to the mold the resultant energy absorbed is increased exponentially. Thus the coil design for induction heating is complex and requires significant experimentation with design and process parameters. Additionally, the manufacturer of thin wall mold systems is less expensive, less complex and more repeatable than RF generator systems. Thin wall molds may be easily reproduced by electroforming, stamping or machining. And the material selection for use in the making of the mold is not as critical as the material selection for molds used in the RF induction machines which requires a certain type of metal. In the RF induction process, it is critical to understand the ferrous content in the base metals used to make the molds. Certain grades of metal will be activated to generate heat in the mold by the RF energy readily while another grade may not generate the heat necessary to melt the moldable material in the RF activated mold. It is typically cautioned during the initial set-up of the RF machine that the mold should not get too much energy or it can heat beyond the use temperature and the mold characterization will be changed. If this should happen, the process parameters may not be the same the next time it is set-up. Excess heat may cause the metals' molecular structure to change and it may react to the RF energy differently. Thus the heat generated by the mold may be different the next time the same parameters are used on the RF machine set up requiring additional process development.

Additionally, some embodiments of the heat source subsystem may more selectively control heat migration and more uniformly control the heating and cooling than solutions such as using a hot air gun as a heat source. The present systems and methods may incorporate heat dams to engage the thermal transfer molds along their length to influence and control where the heat is transmitted in the mold. Using a hot air gun provides limited control as to where the heat is applied and therefore the heating method is inconsistent and unreliable. Without using a heat dam or insulative barrier, the heat may travel the length of the thermal transfer mold and can cause the moldable material to swell and lock itself within the mold preventing the area of the plastic tube that needs to be formed to the desired shape to properly enter completely into the mold and properly pack the mold.

Embodiments of the disclosed heat source subsystem are configured to stably control and/or uniformly control the heating of the thermal transfer mold which in turn is able to stably and uniformly control the heating of the moldable material in the thermal transfer mold. Stable control is defined as how well a temperature is maintained for a certain period of time. In some embodiments, the heat source subsystem is able to stably control the temperature of the heat block assembly with the PLC so that the temperature of the heat core is within a temperature range of plus/minus 20 degrees Fahrenheit of the predetermined temperature for a temperature time period of more than one half of a second. In some embodiments the temperature range is less than plus/minus 20 degrees such as, but not limited to, 15 degrees, 10 degrees, 7 degrees, 5 degrees or 2 degrees. In some embodiments, the temperature time period for any of the temperature ranges may be more than one half of a second such as, but not limited to, more than 1 second, 3 seconds, 10 seconds, one half of a minute, several minutes and more than an hour. Uniform control is defined as how consistent the temperature of one portion of a material compares to the temperature of another portion of that material. Uniform control of the heating of the thermal transfer mold is able to be provided through the use of the heating element, the heat core, the use of the thermal transfer mold and the mating of the thermal transfer mold in the mating portion of the heat core. By using one or more heating elements capable of providing a uniform temperature to the heat block, the heating element is able to provide a uniform heat across and through the heat block assembly and allow a uniform transfer of heat to the heat block. By using a heat block and heat core made from a material with uniform heat transfer properties, the heat core provides uniform heat across and throughout the mating portion of the heat core. By using a thermal transfer mold made from a material with uniform heat transfer properties, the thermal transfer mold is able to provide uniform heat across and throughout the portion of the thermal transfer mold used to mold the moldable material. And the mating of the portion of the thermal transfer mold with the mating portion of the heat core uniformly transfers the heat from the heat core to the thermal transfer mold. In some embodiments, the uniform control of the heat transfer provides temperatures in portions of the heat core and the temperature transfer mold, in the areas intended to be controlled, such that the temperature of no point of a portion of the areas intended to be controlled is greater than a temperature uniformity range of 30% from the temperature of a point at another portion of the areas intended to be controlled. The temperature uniformity range may be less than 30% such as but not limited to less than 25%, 20%, 18%, 15%, 12%, 10%, 8%, 5%, 3% or 1%. The areas intended to be controlled of the heat core are the mating portions and those portions/areas of the heat core configured to transfer heat to the heat transfer mold. Temperature uniformity ranges similar to those of the heat core may be used for the thermal transfer mold. The areas intended to be controlled of the thermal transfer mold may be those portions/areas of the thermal transfer mold that are configured to transfer heat to the moldable material so that the moldable material can be shaped.

To illustrate an example of the stable and uniform control features of the heat control subsystem, an example embodiment is described. In this example embodiment, the PLC is set to provide a predetermined temperature to the heat block of 350° F. The properties of the PLC, the heating element (or heater cartridge), the heat block and the heat core provide a temperature at the exposed portion of the heat core of 340° F. (Although this temperature is different than the predetermined temperature of the PLC, this is also a predetermined temperature calibrated to reflect the difference in temperature from the PLC setting.) The stable control controls the portion of the heat core heating the thermal transfer mold such that the temperature range of the heat core is within 5° F. of 340° F. for a duration of 12 seconds (of a 22 second cycle). The uniform control keeps all portions of the heat core configured to transfer heat to the thermal transfer mold at a stable temperature. For example, if the portion exposed to accept the thermal transfer mold is at a temperature of 340° F. and the temperature uniformity range is 10%, the furthest point within the recess of the heat core to accept the tip of thermal transfer mold could be 306° F. or 374° F. By stably and uniformly controlling the heat core, the thermal transfer mold, when mating with the heat core, can be similarly stably and uniformly controlled. By stably and uniformly controlling the thermal transfer mold, the moldable material, when inserted in the mold, can be similarly stably and uniformly controlled.

Embodiments of the cooling source subsystem may comprise any method of cooling the thermal transfer mold. One example embodiment of the cooling source subsystem comprises of a nozzle designed to pin point or fan out the flow of cooling air.

In some embodiments, the cooling source subsystem is capable of providing a uniform cooling by the use of compressed air or from a cold air chilling system. In another possible embodiment is to incorporate a vortex air cooler or spray a mist of water directly onto the mold to set the shaped catheter.

Some embodiments of the cooling source subsystem are able to stably and uniformly control the cooling of the thermal transfer mold using the features and configurations described above for heating. As described above for the heating of the heat core and the thermal transfer mold, the heat core, thermal transfer mold and the mating features of the two are also able to provide stable and uniform control of the cooling when the temperatures are reduced. This stable and uniform control of the cooling is beneficial to help the moldable material cool down and solidify after heating.

Some embodiments of the moldable material shaping systems provide for flaring an end of the moldable tube to allow for an insert molded fitting or to have a taper to aid in the introduction of guidewires or smaller catheters. It is an object of these embodiments to utilize thin wall mold technology for the purpose of flaring the ends of a plastic tube. The thermal transfer molds for these embodiments may be formed by a process such as electroforming, machining or deep draw metal forming. One preferred method of forming is electroforming because it's an electro activated plating process and is highly detailed to allow making molds without having a secondary polishing process. This process also allows the molds to be made with a shiny inside surface or with a shiny pitted surface to allow for non-stick surfaces. The smaller size tubes will require a smaller and shorter length tip mold. It would be expected the mold wall thickness to be thinner than used in a thermal transfer mold for a larger tube/catheter.

Figure 8:
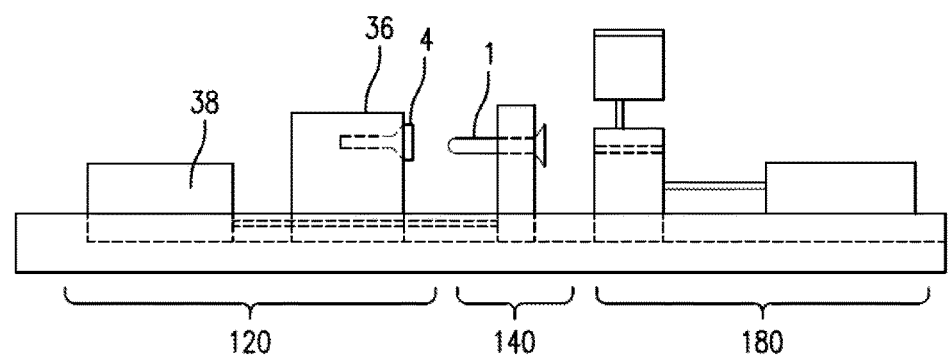
FIG. 8 illustrates one alternative embodiment of a moldable material shaping system wherein the gripper assembly and thermal transfer mold are slidably positioned to contact the stationary heat core to perform the forming operation.

Some embodiments of the moldable material shaping system provide for a stationary heat source subsystem. FIG. 8 shows an example embodiment of the moldable material shaping system utilizing the same components depicted in FIG. 1 but with the heat source subsystem 120 comprised of heating block 36 and heat core 4 stationary. In this embodiment, the mold subsystem 140 is now slidably positional towards the heat source subsystem 120 by means of connection to a motor and slide assembly 38 which is controlled by a control box (not shown). The gripping subsystem 180 holding the moldable material (not shown) is used in a similar manner as depicted in FIG. 1 to push the material into heated mold 1 to soften and reshape it. As shown, the slide assembly 38 can be designed to be hidden under the top plate of the moldable material shaping system and does not have to be on the surface.

Figure 10A:
FIGS. 10A-10F illustrate multiple embodiments of a moldable material shaping system and method joining tube to tube.
Figure 10B:
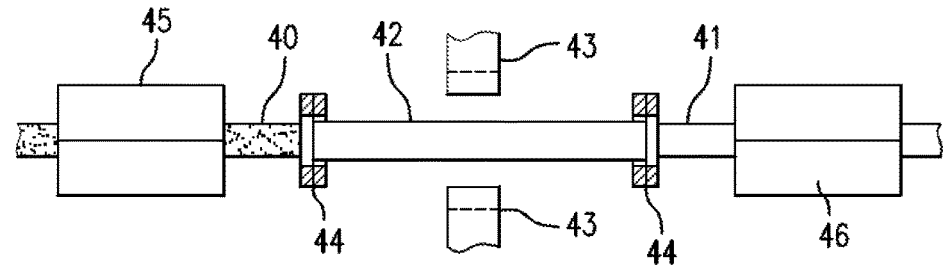
Figure 10C:
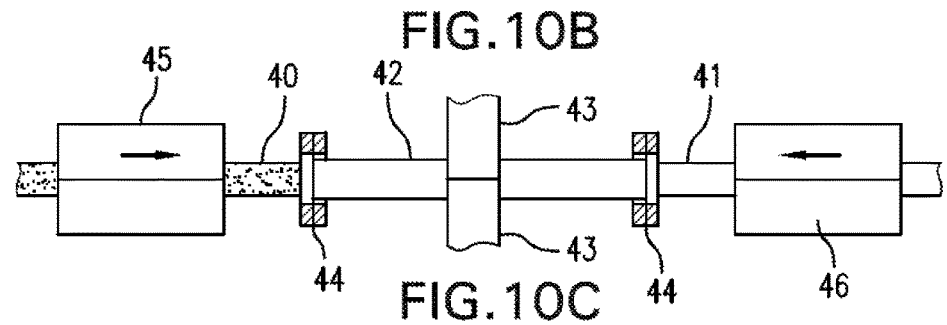
Figure 10D:
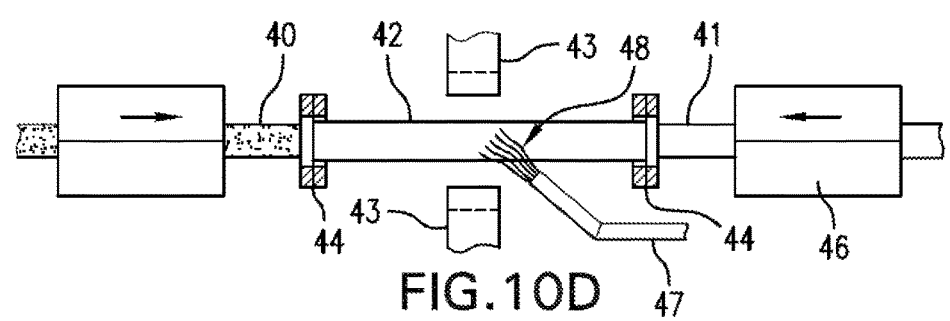
Figure 10E:
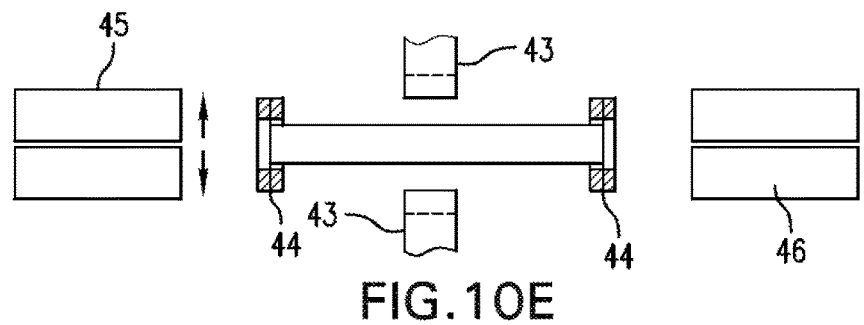
Figure 10F:
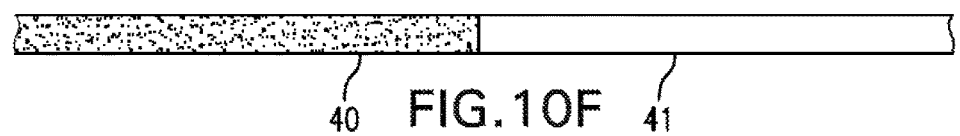

Some embodiments of the moldable material shaping system provide for joining two separate moldable materials into one piece. This joining of two separate types of extrusion into one tube is a process that may be used to obtain sections of a moldable material, such as a catheter, that has different properties across different sections of the material. This may allow for what is known in the industry as a variable stiffness catheter. FIGS. 10A-10F illustrate an example of how this embodiment of the moldable material shaping system process may join materials using the thin wall mold technology. The sequence is depicted from FIG. 10A to FIG. 10F. FIG. 10A shows two separate moldable components 40 and 41, such as tubes. FIG. 10B shows two separate tubes inserted inside the thermal transfer mold 42. FIG. 10C shows tube grippers 45 and 46 closed and pushing towards each other and the moveable heat cores 43 are positioned onto the thermal transfer mold 42 to transfer the heat melting the ends of tubes 40 and 41 forming a single tube. FIG. 10D shows the moveable or positional heat cores 43 moved away from the thermal transfer mold 42 and the cooling subsystem 47 starts cooling the thermal transfer mold 42 with air 48. FIG. 10E shows the joined tubes removed from the mold. FIG. 10F shows the joined tubes (40 and 41) as a single joined tube. In joining tubes together, mandrels may have to be inserted into the tubes to keep any lumens within the moldable material open and the mandrels may be removed afterwards when the thermal fused joint has cooled.

Some embodiments of the moldable material shaping systems may incorporate split moveable or positional heat cores that can be moved or positioned to be in proximity or contact with a thermal transfer mold or die and subsequently removed for the purpose of heating the mold to join two or more individual plastic tubes or rods together. The moveable or positional heat core may be mounted onto a heat insulating material to prevent migration or heat loss and is designed to hold the temperature stable using a control subsystem with a temperature monitoring system. This control subsystem may allow the heating elements to maintain the appropriate heating temperatures for the various temperatures needed for melting or softening of the moldable components. There is sometimes a need to control the temperature to its highest or lowest melting temperature of the moldable material to allow for specific material molecular changes. Embodiments of the split moveable heat cores may also be used to sink or laminate multiple layers of materials to be joined as one.

Figure 11A:
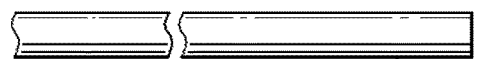
FIGS. 11A-11E illustrate multiple embodiments of a moldable material shaping system and method for necking, sinking or laminating a moldable component.
Figure 11B:
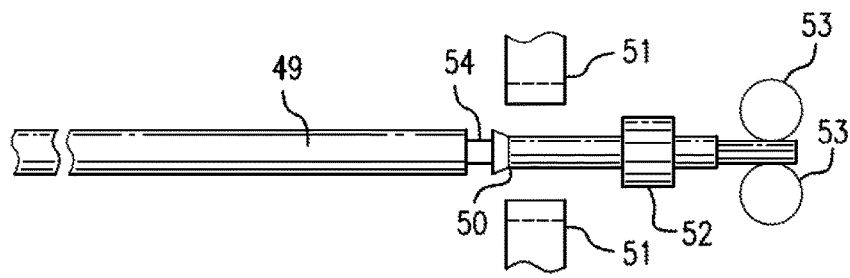
Figure 11C:
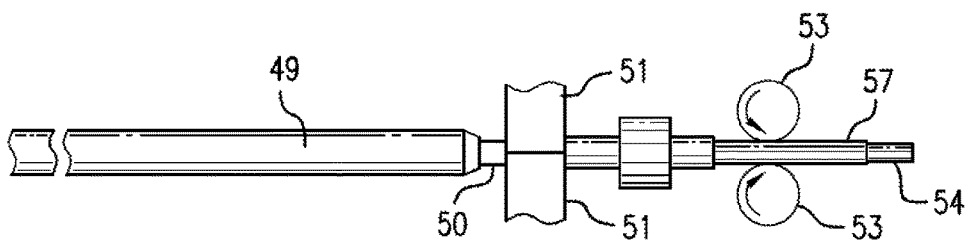
Figure 11D:
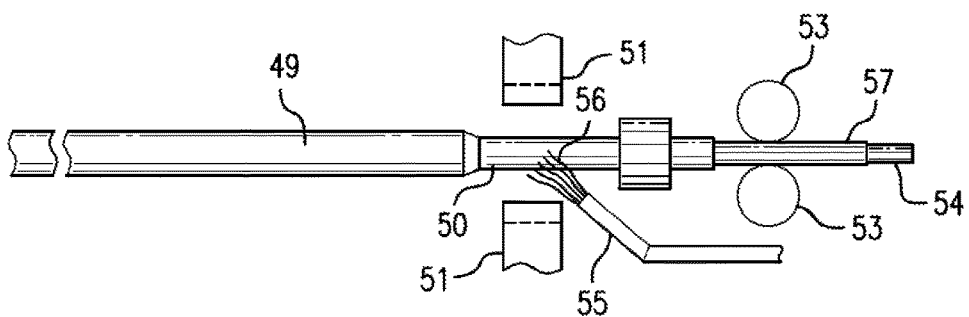
Figure 11E:
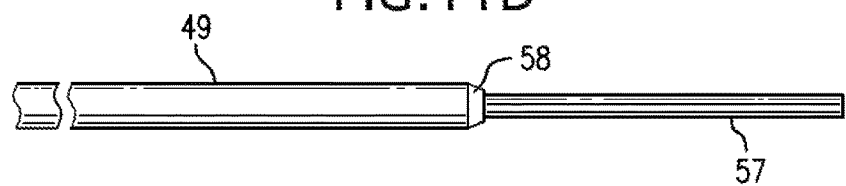

Some embodiments of the moldable material shaping system may be used to neck the moldable component. FIGS. 11A-11E shows one embodiment of the moldable material shaping system used to neck the moldable component. FIG. 11A depicts a tube 49, as a moldable component with a starting dimension. FIG. 11B shows a thin wall necking mold 50 secured by a insulated die holder 52, heat cores 51 in start position and pulling rollers 53 positioned on output side of necking die 50. FIG. 11B also shows tube 49 that is to be necked down with an internal sizing mandrel 54 sized to retain desired finished tube internal diameter which is removed from tubing when resizing is complete. FIG. 11C shows necking step in process with heat cores 51 in contact with thin wall necking die 50 with tube 49 and internal sizing mandrel 54 in process of being heated and pulled through necking mold 50 by puller wheels 53. FIG. 11D shows heat cores 51 retracted from necking mold 50 while puller wheels 53 are stopped with cooling nozzle 55 activated and blowing air 56 on to necking mold 50 to cool mold 50 and tubing 57 in its final dimension. FIG. 11E shows deformed, necked, tube 58 removed from necking mold 50 and with internal sizing mandrel 54 removed from the tube.

Some embodiments of the moldable material shaping system incorporate split moveable heat cores to be moved into proximity or contact and subsequently removed from the proximity or contact with a thermal transfer mold or die for the purposes of necking a tube from a starting diameter to a smaller diameter.

Some embodiments incorporate more than one mold or die into the system to enhance throughput of the process and improving the efficiency. In comparison to RF induction machines, the setting up of multiple tipping molds and balancing the process parameters will be simpler to accomplish utilizing the thin wall thermal transfer moldable material shaping system due to a stable and uniform heating and transfer system. In RF solutions, the impedance of two coils and the second mold positioning has to match to the first mold. Use of two molds is often not recommended by the manufactures of the RF induction generators.

Figure 9A:
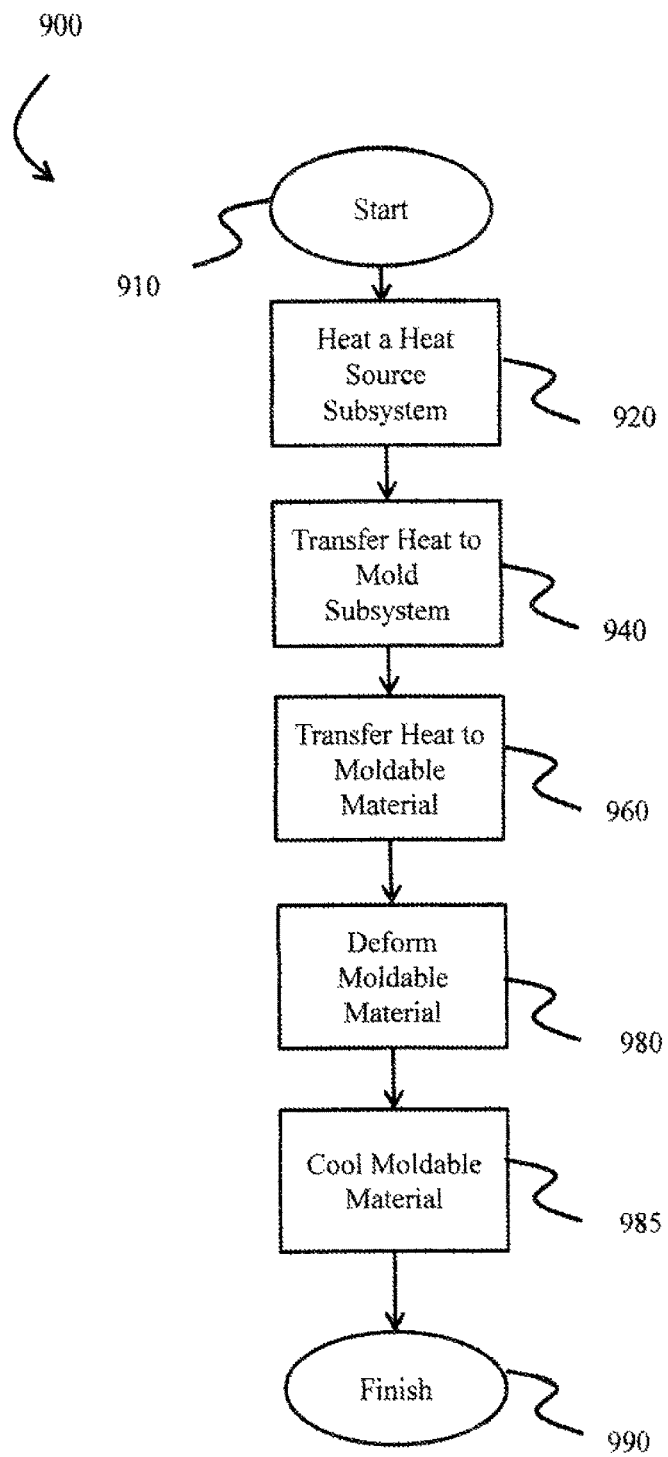
FIG. 9A illustrates the process flow of one example embodiment of methods of using a moldable material shaping system.

One Embodiment of Moldable Material Shaping Methods:

FIG. 9A depicts a general process flow for using the moldable material shaping systems. It is understood that there are other possible process sequences that can be employed with this apparatus. Stepping through the general process of 900, the process is initiated with step 910 of turning on the main power 26 to the system as shown in FIG. 5. This step is followed by step 920 by activating the heat on power switch 22 as shown in FIG. 5 applying heat to the heat source subsystem 120 as shown in FIG. 1. After reaching preset temperature, step 920 is followed by step 940 transferring heat from heat source subsystem to mold subsystem 140 as shown in FIG. 1 by moving heat source subsystem 120 to be in contact with mold subsystem 140 for a predetermined duration. Step 940 is followed by step 960 transferring heat from mold subsystem to preloaded moldable material previously positioned inside heat transfer mold. After a predetermined heating duration to heat moldable material inside transfer mold, step 960 is followed by step 980 to deform moldable material by activating gripper subsystem 180 shown in FIG. 1 pushing moldable material into transfer mold deforming moldable material to conform to internal shape of transfer mold. After a predetermined duration to deform moldable material, step 980 is followed by activating step 985 cooling moldable material. Step 985 retracts heat source subsystem 920 from mold subsystem 940 and activates cooling source subsystem 160, as shown in FIG. 1, for a predetermined duration to cool moldable material stabilizing newly molded material shape. Step 990 completes general process 900 when reshaped molded material is removed from transfer mold.

Figure 9B:
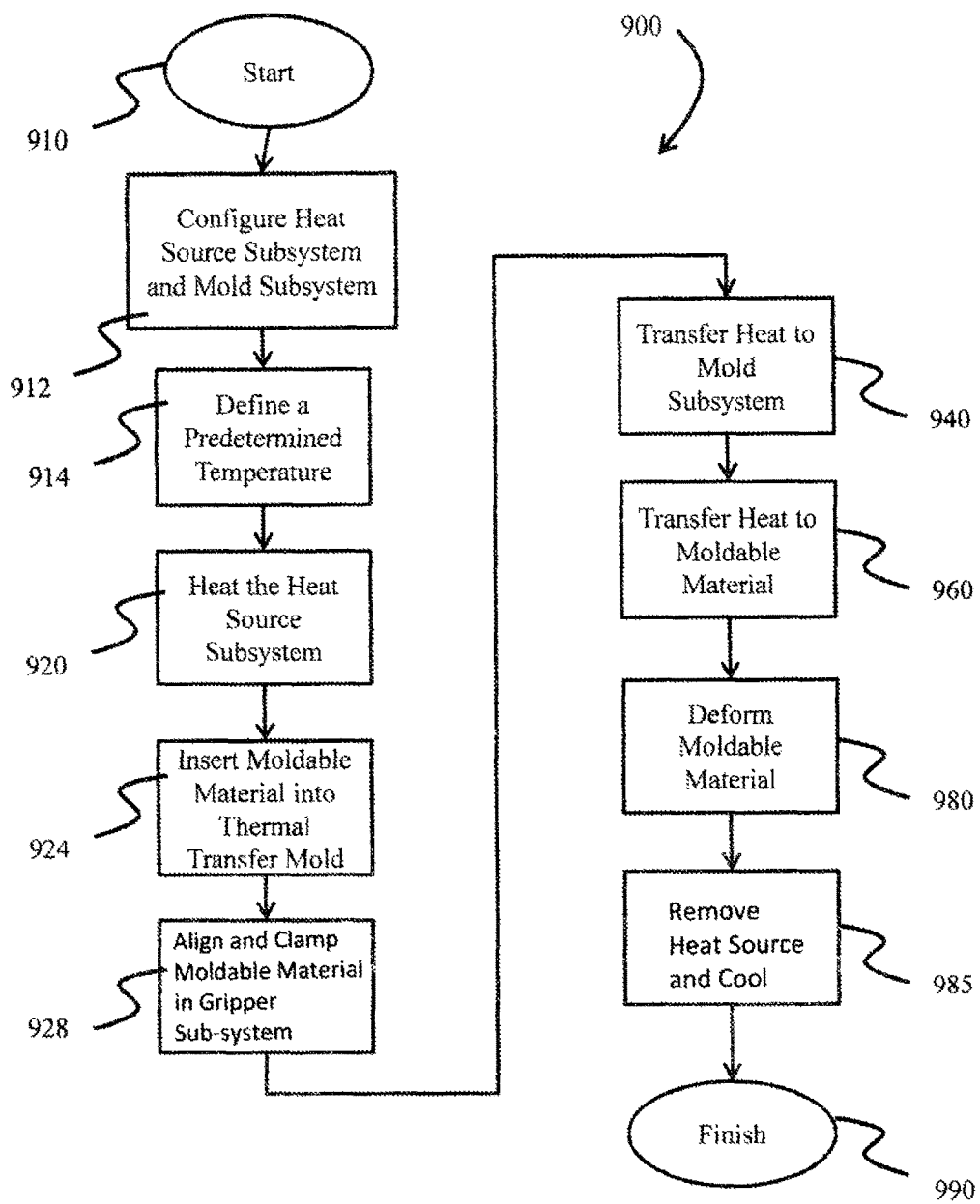
FIG. 9B illustrates the process flow of one example embodiment of methods of using a moldable material shaping system.

FIG. 9B depicts an example process flow for using the moldable material shaping systems. Stepping through this example process of 900, the process starts with step 910 of turning on the main power 26 to the system as shown in FIG. 5. This step is followed by step 912 by setting up the moldable material shaping system as shown in FIG. 1 with the desired heat core 4, appropriate thin wall heat transfer mold 1 and the material gripper 7. Step 912 incorporates setting the gripper pressure to hold moldable material for example at 40 psig, setting moldable material advancement for example to 1 cm by positioning start and finish mechanical stops (not shown) and dwell speed for example to 1 mm/sec to introduce the material into transfer mold 1. This step is followed by step 914 determining a temperature to soften the moldable material by referencing moldable material supplier specifications. For example, 350° F. for polyethylene. Step 920 initiates heat source subsystem to a predetermined temperature by activating heat on switch 22 and temperature set point as shown in FIG. 5 and allow heat source subsystem time to reach set temperature. Step 924 positions the moldable material 99 into the thermal transfer mold 1 as shown in FIG. 15. As shown in step 928 moldable material is aligned and clamped into gripper 7 as shown in FIG. 15. Step 940 starts the forming process by activating the start button 91 as shown in FIG. 5. This will automatically advance the heat source subassembly engaging the heat core 4 as shown in FIG. 15 to the heat transfer mold 1 initiating step 960 transferring heat through heat transfer mold to moldable material 99 (FIG. 15) positioned inside heat transfer mold. Step 980, deforming moldable material, is started automatically. A timer program tells gripper subassembly to advance the moldable material 99 (FIG. 15) and gripper 7 (FIG. 15) into the heat transfer mold 1 (FIG. 15) as programmed filling the mold and shaping the moldable material to internal shape of the transfer mold 1 (FIG. 15). The advancement and final position of the moldable material and heating dwell time is controlled by the PLC using positional stoppers and a timer that were previously set in Step 920. The moldable material will be reshaped as shown in FIG. 15 while the heat transfers from the heat block 5 to the heat core 4 to the heat transfer mold 1 melting the moldable material 99. The dwell setting time will hold the moldable material, such as a catheter, inside the thin wall mold under compression pressure conforming moldable material to the internal shape of heat transfer mold. Step 985 initiates retraction of the heat source subassembly 120 (FIG. 15) at a predetermined time from heat transfer mold 1 (FIG. 15) and may simultaneously initiate a cooling cycle of air (not shown) to be activated by the PLC cooling the mold 1 (FIG. 15) and freezing the reformed material 99 (FIG. 15) to the inside cavity shape of the mold. At the end of the cooling cycle step 985, the gripper subassembly 180 (FIG. 15) will retract removing the reformed material from the heat transfer mold where it can be removed from the gripper. The moldable material shaping system may automatically reset in step 990 for the next moldable material to be formed.

Figure 7A:
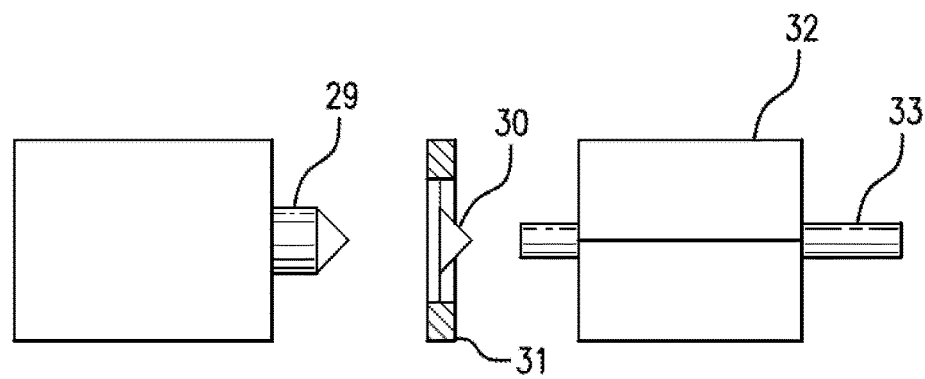
FIGS. 7A-7D illustrate alternative embodiments of the moldable material shaping system to perform flaring of tubes.
Figure 7B:
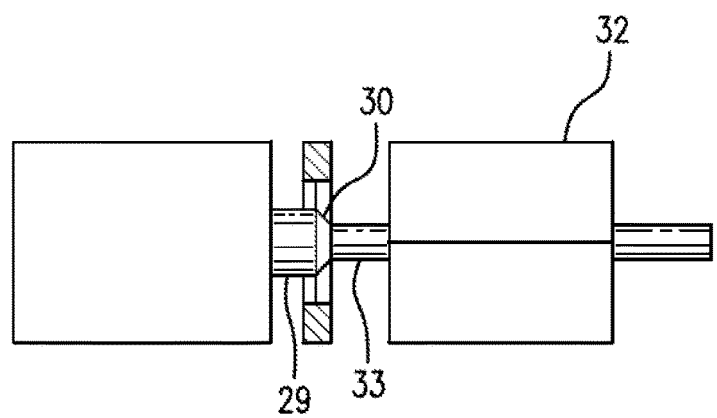
Figure 7C:
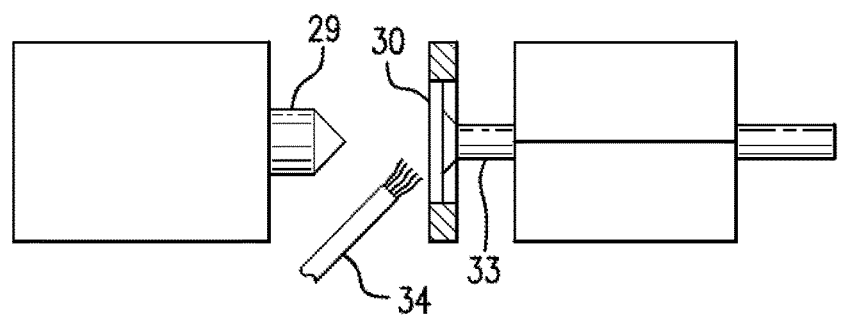
Figure 7D:
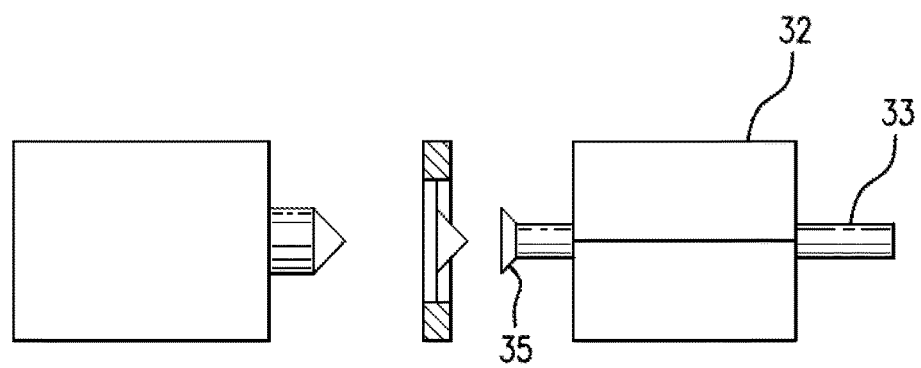

Some embodiments of the moldable material shaping methods provide for a flaring of the tip or end of the moldable material. As shown in FIGS. 7A-7D illustrate one embodiment of the flaring process. FIG. 7A illustrates the set-up of the flaring process using flaring heat core 29 and flaring mold 30 held stationary by insulated mold holder 31. The moldable material 33 is clamped by gripping assembly 32. FIG. 7B illustrates the following sequence for this process as the heat core 29 advances to contact mold 30 as material gripper 32 is advanced to provide contact of moldable material 33 with heated flaring mold 30. FIG. 7C shows heat core 29 withdrawn from contact with flaring mold 30 to allow the cooling of flaring mold 30 by activation of coolant air 34 freezing the flare on the moldable material while remaining in contact with flaring mold 30. FIG. 7D shows the flared shape 35 formed on the tip or end of the moldable material 33.

Some embodiments of the moldable material shaping methods provide for a joining of multiple moldable materials Identified in FIGS. 10A-10F. In these embodiments, FIG. 10A shows two moldable materials 40 and 41 that are to be joined into one part. FIG. 10B shows the joining process comprised of setting up the material shaping unit with two opposing heat cores 43 set to a predetermined temperature, a heat transfer mold 42 attached to insulated mold holders 44 and two moldable material grippers 45 & 46 preset to a gripping pressure holding the two moldable materials 40 and 41 loaded into the heat transfer mold 42. FIG. 10C illustrates the starting of the joining process with the opposing heat cores 43 in contact with the heat transfer mold 42 transferring heat to the heat transfer mold and into the moldable materials while the PLC simultaneously moves the grippers towards the heat transfer molds advancing the two moldable materials together and into the thin wall mold. As the two pieces advance together the heat core transfers the heat into the mold causing both ends to soften and melt together. At the end of the heat cycle, the heat cores retract and cool air is applied to the thin wall mold (FIG. 10D) setting the joint to form one tube assembly. The grippers release the material (FIG. 10E) and the joined material is removed from the mold as shown in FIG. 10F.

Some embodiments of the moldable material shaping methods provide for a draw down (also known as necking) of the tip of the moldable material to a smaller dimension. FIGS. 11A-11E illustrates one embodiment of the necking process. FIG. 11A illustrates a moldable material 49 with a uniform diameter pre-necked. FIG. 11B illustrates the set-up of the necking process using opposing heat cores 51, necking mold 50 held in position by a insulated necking mold holder 52, mandrel 54 positioned inside moldable material 49 and inside the necking mold 50 with roller/puller wheels 53. FIG. 11C illustrates the necking process sequence using opposing heat cores 51 in contact with heat transfer mold 50, necking mandrel 54 inside moldable material 49 inserted into heat transfer mold 50 with mandrel 54 in forced contact and engaged with roller/puller wheels 53. The roller/puller wheels 53 grip necked molded material 57 with inside mandrel 54 pulling molded material into heated transfer mold 50 reducing the outside diameter of the moldable material 49 to the inside diameter of the heat transfer mold 50. FIG. 11D illustrates the completion of the necking process where the roller/puller wheels 53 have been programmed to stop at a predetermined position as controlled by the PLC, retraction of the opposing heat cores 51 from heat transfer mold 50 and activation of air coolant 56 directed by coolant nozzle 55 at the heat transfer mold 50 to cool mold and necked material 57 inside heat transfer mold 50. FIG. 11E illustrates the finished necked moldable material removed from heat transfer mold 50 and with mandrel 54 removed. Completed item is comprised of the original un-necked section 49, necked section 57 and transition section 58 between un-necked section 49 and necked section 57.

Figure 14A:
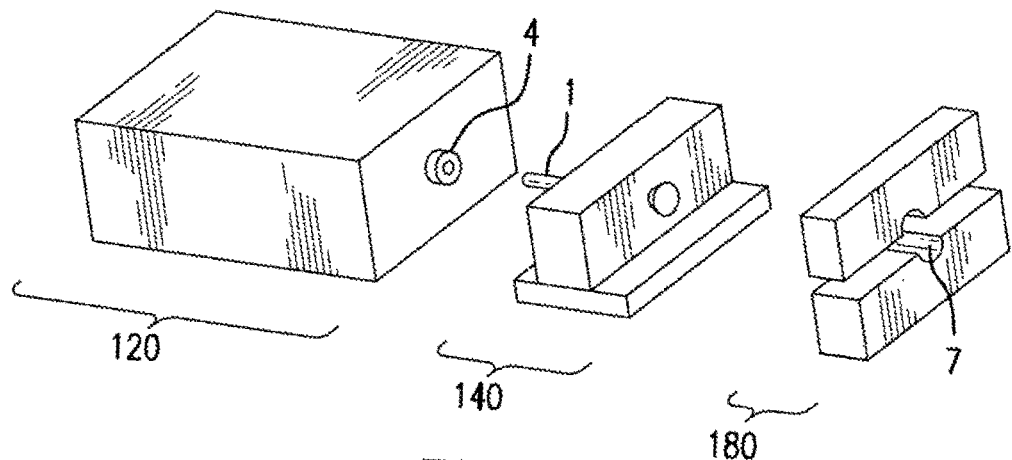
FIG. 14A illustrates one embodiment of a moldable material shaping system having a single thermal transfer mold.
Figure 14B:
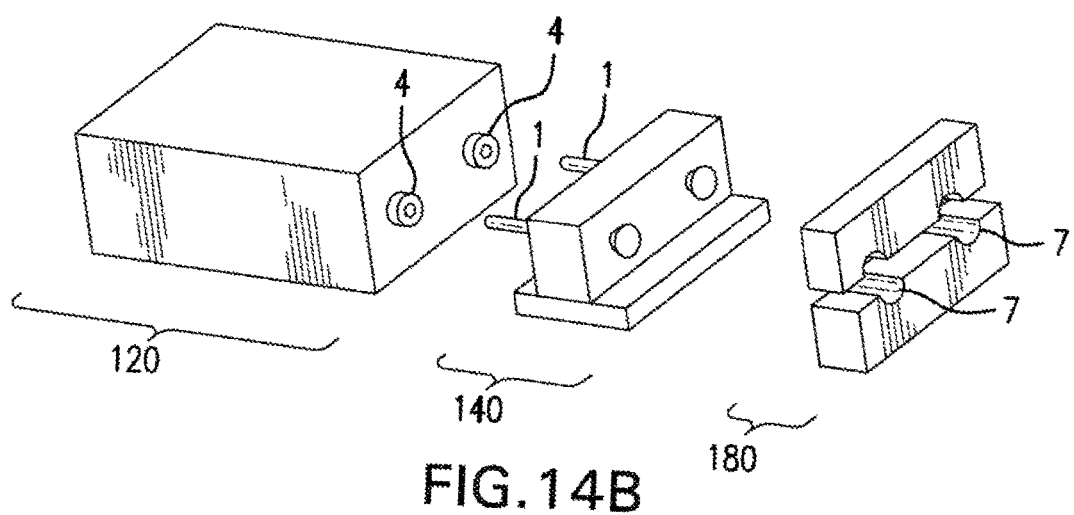
FIG. 14B illustrates one embodiment of a moldable material shaping system having multiple thermal transfer molds.

Some embodiments of the moldable material shaping methods provide for the use of a single mold or multiple molds. Single mold systems are more commonly used for development purposes whereas multiple mold systems are commonly used for production purposes. As shown in FIG. 14A illustrates a single mold system comprised of a heat source subassembly 120 with a single heat core 4, a single heat transfer subassembly 140 with a single thermal transfer mold 1 and a single gripper subassembly 180 with a single gripper 7. As shown in FIG. 14B, in these embodiments, the process of using multiple molds comprises having the heat block assembly subassembly 120 with multiple heat cores 4, a heat transfer subassembly 140 with multiple heat transfer molds 1 and a multiple gripper subassembly 180 with multiple grippers 7 designed to grip multiple pieces of a moldable material, such as multiple catheters. The multiple mold systems may also be comprised of multiple single mold system configurations as shown in FIG. 14A incorporated into one machine (not shown). They can be advanced simultaneously or individually into the heat transfer molds. The heat block assembly and the heating element are designed to maintain the temperature and supply sufficient energy to transfer the heat to the heat cores. The operation of shaping multiple tubes is similar to the operation of shaping a single tube. In a possible scenario with dual tipping, one material is inserted into the mold and gripped into position. The second mold is loaded with the second material and gripped in the second gripper that is adjacent to the first mold. When both pieces of moldable material are positioned correctly, the operator will start the cycle and both tip thermal transfer molds with moldable materials will be advanced into the heat source sub-assembly and both molds will be heated simultaneously. At the end of the heat cycle both thermal transfer molds with moldable materials may be withdrawn and cooled by the cooling system. Each gripping system can be individually released to allow removal of the moldable materials. The operation can be repeated as necessary.

Some embodiments of the moldable material shaping methods provide for the use of split positional heat cores. In these embodiments, the process uses split positional heat cores comprised of two or more separate heat cores designed to slide apart and close together simultaneously around the thermal transfer mold during the heat transfer cycle. In these embodiments, the heat cores have a heat chamber sized to mate with and/or receive and heat a portion of the thermal transfer mold and the portions of the moldable materials received in the thermal transfer mold. The positional heat cores are positional between a heating position and a cooling position whereby the heating position places the heat chamber in a proximity of the thermal transfer mold such that the heat chamber heats the portion of the thermal transfer mold and the cooling position places the heat chamber away from the thermal transfer mold whereby the thermal transfer mold is cooled. The PLC allows for programmed sequences to slide, clamp and heat as described in previous section. FIGS. 10A-10F and the related discussion illustrate an example embodiment of split positional heat cores. In some embodiments, the positional heat cores may be moveable heat cores.

Embodiments of the Moldable Material Shaping System in Operation for Tipping Catheters:

For illustration purposes and not for limitation, example embodiments of the moldable material shaping system to be used in shaping the tips of catheters will be described in operation.

Referring to FIG. 1, to operate this example embodiment, the moldable material to be shaped, for example a plastic catheter (not shown), is placed into thermal transfer mold 1 and gripper 7 and securely clamped by activating a motor or pneumatic clamp 8. The hot heat core 4 is slid by activating motor 9 into a position of appropriate contact with the thermal transfer mold 1 for a predetermined period of time to rapidly heat the plastic catheter (not shown) inside thermal transfer mold 1. After the required time period to heat and soften the plastic part, the gripper 7 holding the moldable catheter (not shown) is slid towards the mold 1 by activation of motor 10 driving the softened moldable catheter into the mold 1 conforming to the inside shape of mold 1. Positional heating block assembly 5 with heat core 4 is retracted away from the tip mold 1 followed by activation of the cooling nozzle 11 resulting in rapid cooling of mold 1 and internal plastic catheter (not shown) freezing the catheter tip into its desired form.

Figure 2B:
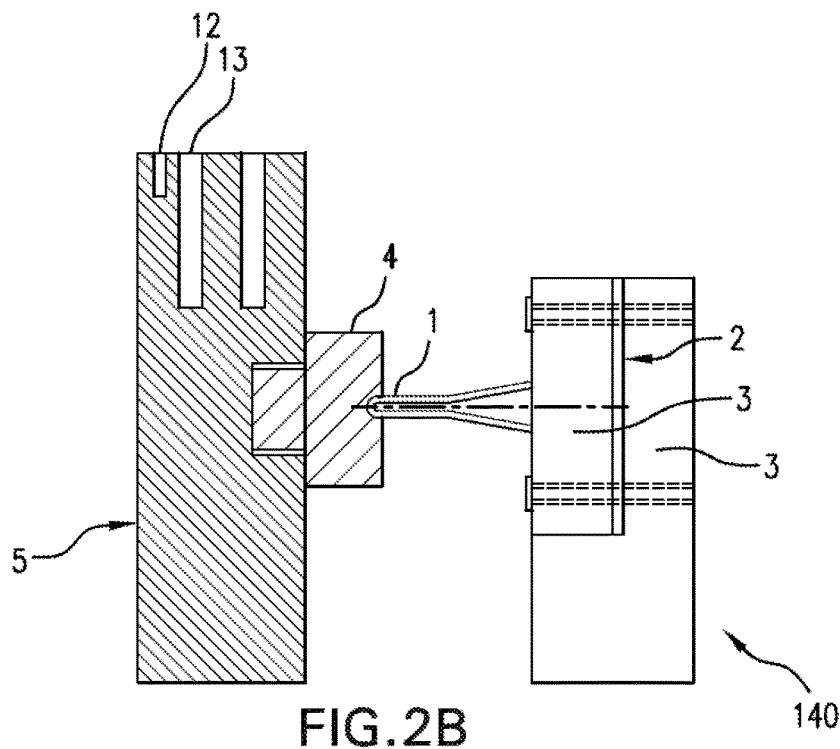
Figure 2C:
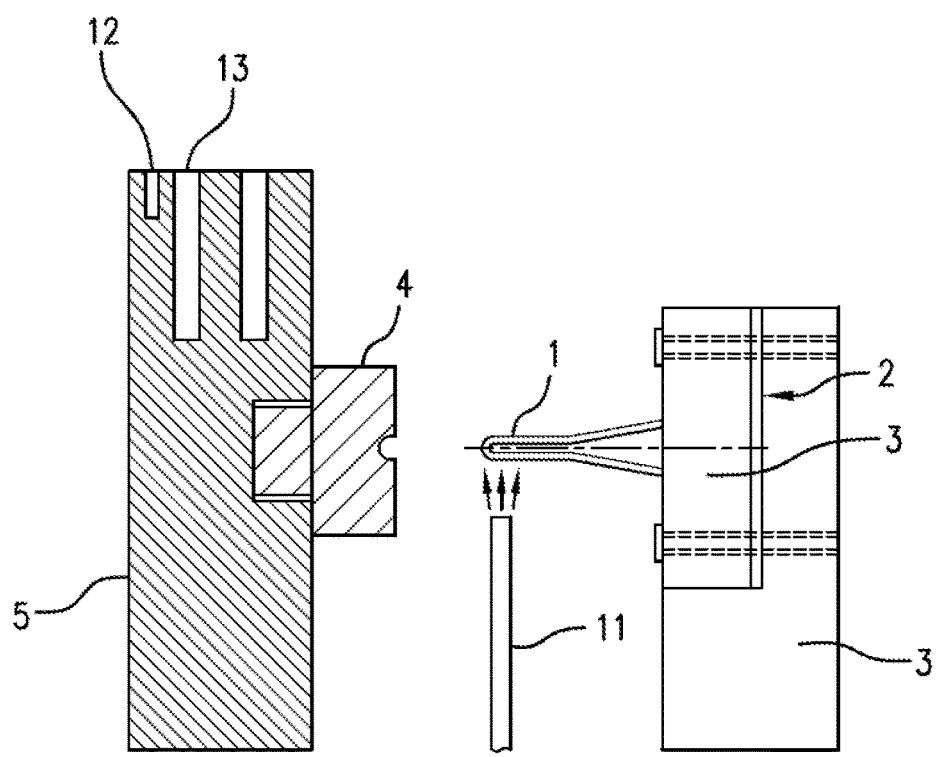

Referring now to FIGS. 2A-2B, shown is a sectional detail of the sequence of one embodiment of the moldable material shaping process, here for forming a catheter tip. FIG. 2A shows a thin thermal transfer mold 1 connected to insulated mold holder 2 and securely connected to stationary mold clamp 3. FIG. 2A shows the starting position of the thermal transfer mold 1 in relation to the heat core 4. FIG. 2B shows the positional block assembly 5 moved to provide for the heat core 4 to contact the thermal transfer mold 1 to heat the thermal transfer mold 1 and plastic part (not shown) inside the thermal transfer mold 1. FIG. 2C shows heat core retracted from thermal transfer mold 1 allowing for cooling of tipping mold 1 by cooling nozzle 11 blowing air to cool thermal transfer mold 1 and plastic part (not shown) inside thermal transfer mold and setting the shape of the plastic part tip. Depicted in FIGS. 2A, 2B and 2C are the heat core 4 securely connected to positional heating block assembly 5 containing thermocouple 12 and resistance heaters 13 which connect to control box 6 in FIG. 1. FIG. 2b shows thermal transfer mold 1 engaged within matching heat core 4 cavity.

FIGS. 7A-7D illustrate one example embodiment and process sequence to perform flaring of tubes or catheters using similar thin wall thermal transfer mold technology. FIG. 7A depicts the starting position of the flaring process which is comprised of a mating heat core 29, thin wall flaring thermal transfer mold 30 (cross section) with insulated mold holder 31 (cross section) around flaring mold to prevent heat transfer to stationary mold clamp (not shown), a moldable material tubing gripper 32 with a plastic tube 33 clamped in place in preparation for flaring. FIG. 7B depicts the heat core 29 in contact with flaring mold 30 (shown in cross section) to heat plastic tube 33 in contact with flaring mold 30. FIG. 7C depicts heat core 29 retracted from flaring mold 30 and cooling nozzle 34 blowing cool air to back side of flaring mold 30 to rapidly cool mold and flared end of plastic tube 33 setting the flared shape. FIG. 7D depicts the completed process with flared end 35 of plastic tube 33 still held by gripper 32.

FIGS. 10A-10E illustrate one embodiment of a plastic tube to plastic tube joining process (also referred to as "butt joining" or "lap welding") utilizing the catheter shaping system. FIG. 10A depicts a first tube 40 that is to be joined to a second tube 41. FIG. 10B shows tubes 40 and 41 positioned into a thermal transfer mold 42 (which acts as a joining die) which is connected at the ends to an insulative material 44 and held in position by mold clamps (not shown) positioned around the insulative material 44. The first tube 40 is held by tube clamp 45 and the second tube 41 is held by tube clamp 46 in a starting position with heating cores 43 retracted from joining die 42. A mandrel (not shown) may be placed inside tubes 40 and 41 to maintain an internal dimension as required during the joining process. FIG. 10C shows heating cores 43 in contact or mating with thermal transfer mold 42 and tube clamps 45 and 46 activated to provide movement to push tubes together inside the thermal transfer mold 42 to melt and join tubes 40 and 41 together. FIG. 10D shows heating cores 43 retracted from thermal transfer mold 42 while cooling nozzle 47 is activated blowing air 48 at heated portion of thermal transfer mold to cool tubes 40 and 41 inside thermal transfer mold 42. FIG. 10E shows tube clamps 45 and 46 in open state with joined tubes 40 and 41 removed from joining die ready for new parts to be joined. FIG. 10E depicts tubes 40 and 41 joined together.

FIGS. 11A-11E step through one embodiment of the necking process where the need is for a smaller diameter section or for laminating a layer of material or braid over a section of a tube needing re-enforcement (not shown). FIG. 11A illustrates a tube requiring a smaller uniform diameter at the tip. This is a sequence of the draw down process. In FIG. 11B, the tube 49 is fitted with a mandrel 54 positioned into the thermal transfer mold 50 and the tube assembly is positioned and clamped in a roller assembly 53. In FIG. 11C the mold is heated by positional or moveable heat cores 51 as the mold 50 is heated, the rollers assembly will clamp and draw the tube 49 and mandrel 54 through the thermal transfer mold 50 at a controlled specific speed. In this draw down process, the tube will resize to the inside diameter of the thermal transfer mold. FIG. 11D illustrates the cycle cooling the thermal transfer mold 50. As the tube is withdrawn from the mold it will be held in the necking fixture until it cools. FIG. 11E shows the tube drawn down to a smaller size after it's withdrawn from the mold. The taper transition 58 is noted on the tube.

The operation of using multiple moldable components using the moldable material shaping system comprises having the moldable material shaping system designed with multiple components such as multiple thermal transfer molds and multiple gripping subsystems with multiple cooling source subsystems. The need to have multiple thermal transfer molds is more for a production situation and would need to be of the same size and shape. The heat core assembly may be designed to have two or more heat cores instead of one. The gripping subsystems may require two or more separate systems and be designed to work simultaneously or work independently of each other.

Figure 12A:
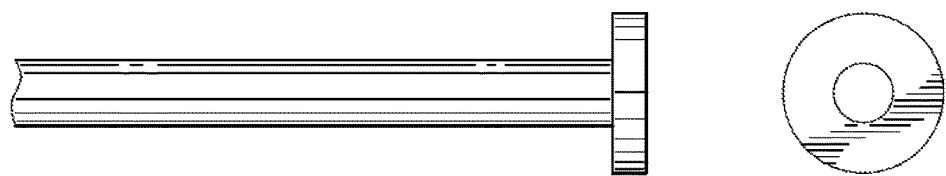
FIGS. 12A and 12B illustrate alternative tip configurations using the moldable material shaping systems and methods.
Figure 12B:
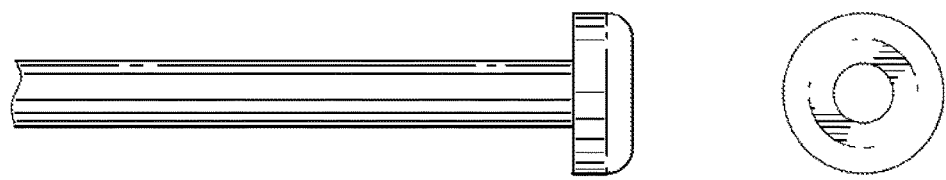

FIG. 12 illustrates alternative formed tip configurations using adaptations of the thermal transfer mold technology. FIG. 12A shows a flange formed on the end of a tube and FIG. 12B shows a knob or head formed on the end of a tube. The thermal transfer molds employed to form tip configurations illustrated in FIGS. 12A and 12B require alternative mold designs utilizing the thin wall transfer molding technology than would be used to form a typical tapered tip shape.

The foregoing is considered as illustrative only of the principles of embodiments disclosed herein. Further, since numerous modifications and changes will readily occur to those skilled in the art, it is not desired to limit embodiments disclosed herein to the exact construction and operation shown and described, and accordingly, all suitable modifications and equivalents may be resorted to, falling within the scope of embodiments disclosed herein. Although embodiments disclosed herein have been described in the above forms with a certain degree of particularity, it is understood that the present disclosure has been made only by way of example and numerous changes in the details of construction and combination and arrangement of parts may be resorted to without departing from the spirit and scope of embodiments disclosed herein.

We claim:

1. A moldable material shaping system for shaping a plastic tube, said system comprising:
   a thermal transfer mold having an internal cavity configured to receive a moldable material;
   the internal cavity further comprising an internal mold shape;
   a heat source subsystem configured to receive a portion of the thermal transfer mold;
   the heat source subsystem is configured to receive and release the portion of the thermal transfer mold during operation of the system;
   the thermal transfer mold comprises a single piece thermal transfer mold made from a uniform heat conductive material;
   the thermal transfer mold configured to uniformly transfer heat from the heat source subsystem to the portion of the thermal transfer mold and uniformly heat the moldable material received in the portion of the thermal transfer mold thereby reshaping the moldable material to a deformed moldable material shape conforming to the internal mold shape;
   the portion of the thermal transfer mold further comprises a wall having a wall thickness within a range of between 0.065 inches and 0.004 inches;
   the heat source subsystem is not a Radio-Frequency (RF) heat source;
   the heat source subsystem comprises a heat core configured to transfer heat to the portion of the thermal transfer mold;
   the heat source subsystem further comprises an activating motor configured to move the heat source subsystem to receive and release the portion of the thermal transfer mold during operation of the system;

the heat core is positional relative to the thermal transfer mold whereby the heat core may be moved to not transfer heat to the portion of the thermal transfer mold; and the moldable material shaping system further comprises a cooling source subsystem configured to cool the portion of the thermal transfer mold when the portion of the thermal transfer mold is released from the heat source subsystem.

2. The moldable material shaping system of claim 1 wherein the portion of the thermal transfer mold further comprises the wall having a uniform wall thickness.

3. The moldable material shaping system of claim 1 wherein the portion of the thermal transfer mold further comprises the wall having the wall thickness within the range of between 0.020 inches and 0.008 inches.

4. The moldable material shaping system of claim 1 wherein the thermal transfer mold further comprises a closed distal end.

5. The moldable material shaping system of claim 1 wherein a distal end of the thermal transfer mold further comprises a mandrel coupled to an interior mold shape configured to fit into a distal lumen of the moldable material.

6. The moldable material shaping system of claim 1 wherein a distal end of the thermal transfer mold further comprises a through hole configured to receive a mandrel.

7. The moldable material shaping system of claim 1 wherein the heat source subsystem comprises a convective heat source.

8. The moldable material shaping system of claim 1 wherein the heat source subsystem comprises a conductive heat source.

9. The moldable material shaping system of claim 1 wherein:

the heat source subsystem having a mating portion defined by an entire recess in the heat source subsystem; and the mating portion is configured to circumscribingly receive and be in contact with or in close proximity to the portion of the thermal transfer mold received in the mating portion whereby the heat source subsystem can uniformly heat the portion of the thermal transfer mold received in the mating portion and uniformly heat the moldable material within the portion of the thermal transfer mold received in the mating portion.

10. The moldable material shaping system of claim 1 wherein:

the portion of the thermal transfer mold further comprises the wall having a uniform wall thickness;

the heat source subsystem is configured to stably control the heating of the portion of the thermal transfer mold within a temperature range of less than 5 degrees Fahrenheit for a temperature time period of greater than 5 seconds; and the heat source subsystem is configured to uniformly control the heating of the portion of the thermal transfer mold within a temperature uniformity range such that a temperature in degrees Fahrenheit at one point of the thermal transfer mold is no greater than 20% from a temperature of all other points of the thermal transfer mold.

11. The moldable material shaping system of claim 1 wherein:

the heat source subsystem is configured to stably control the heating of the portion of the thermal transfer mold within a temperature range of less than 2 degrees Fahrenheit for a temperature time period of greater than 2 seconds; and the heat source subsystem is configured to uniformly control the heating of the portion of the thermal transfer mold within a temperature uniformity range such that a temperature in degrees Fahrenheit at one point of the thermal transfer mold is no greater than 10% from a temperature of all other points of the thermal transfer mold.

12. The moldable material shaping system of claim 1 wherein:

the heat core is interchangeable with a second heat core; and the heat core and the second heat core are configured to mate with an external portion of the thermal transfer mold.

13. The moldable material shaping system of claim 1 further comprising:

a mold clamp removably securing a proximal end of the thermal transfer mold to the mold clamp; and an insulation layer positioned between the proximal end of the thermal transfer mold and the mold clamp whereby the heat flow from the thermal transfer to the mold clamp is reduced.

14. The moldable material shaping system of claim 1 wherein the cooling source subsystem provides a cooling source comprised of one selected from a group consisting of:

cooling fins; and heat exchanger coils.

15. The moldable material shaping system of claim 1 wherein the cooling source subsystem provides a cooling source comprised of a moveable split heat sink element configured to be clamped around the thermal transfer mold.

16. The moldable material shaping system of claim 1 wherein:

the cooling source subsystem is configured to stably control the cooling of the portion of the thermal transfer mold within a temperature range of less than 5 degrees Fahrenheit for a temperature time period greater than 5 seconds; and the cooling source subsystem is configured to uniformly control the cooling of the portion of the thermal transfer mold within a temperature uniformity range such that a temperature in degrees Fahrenheit at one point of the thermal transfer mold is no greater than 20% from a temperature of all other points of the thermal transfer mold.

17. The moldable material shaping system of claim 1 wherein the single piece thermal transfer mold is further configured to receive a second moldable material.

18. The moldable material shaping system of claim 1 wherein the heat source subsystem comprises two or more positional heat cores.

19. The moldable material shaping system of claim 1 wherein:

the heat source subsystem comprises two or more positional heat cores; and the positional heat cores are positional between a heating position and a cooling position whereby the heating position places the positional heat cores in a proximity of the thermal transfer mold whereby the positional heat cores heat the portion of the thermal transfer mold and the cooling position places the positional heat cores away from the thermal transfer mold whereby the portion of the thermal transfer mold is cooled.

20. A moldable material shaping system for shaping a plastic tube, said system comprising:
- a thermal transfer mold having a cylindrical internal cavity with a first open end and a second open end;
- the internal cavity comprising an internal mold shape;
- the internal cavity sized to receive a portion of a first moldable material in the first open end and a portion of a second moldable material in the second open end;
- the thermal transfer mold comprises a single piece thermal transfer mold made from a uniform heat conductive material;
- the thermal transfer mold configured to uniformly transfer heat from a heat source subsystem to the portion of the thermal transfer mold and uniformly heat the portions of the first and second moldable materials received in the portion of the thermal transfer mold thereby reshaping the portions of the first and second moldable materials to a deformed moldable material shape conforming to the internal mold shape;
- the heat source subsystem having a heat chamber sized to removably receive and uniformly heat a portion of the thermal transfer mold and uniformly heat the portions of the first and second moldable materials received in the thermal transfer mold;
- the heat source subsystem is configured to receive and release the thermal transfer mold during operation of the system;
- the heat source subsystem comprising two or more positional heat cores;
- the heat source subsystem further comprises an activating motor configured to move the heat source subsystem to receive and release the thermal transfer mold during operation of the system;
- the positional heat cores are positional relative to the thermal transfer mold whereby the positional heat cores may be moved to not transfer heat to the thermal transfer mold;
- the portion of the thermal transfer mold further comprises a wall having a thickness within a range of between 0.065 inches and 0.004 inches;
- the heat source subsystem is not a Radio-Frequency (RF) heat source;
- the positional heat cores are positional between a heating position and a cooling position whereby the heating position places the heat chamber in a proximity of the thermal transfer mold whereby the heat chamber heats the portion of the thermal transfer mold and the cooling position places the heat chamber away from the thermal transfer mold whereby the portion of the thermal transfer mold is cooled;
- a control subsystem configured to control the heat source subsystem whereby the portions of the first and second moldable materials are joined; and
- a cooling source subsystem configured to cool the thermal transfer mold when the thermal transfer mold is released from the heat source subsystem and stabilize the portions of the first and second moldable materials inside the thermal transfer mold to maintain the deformed moldable material shape.

21. The moldable material shaping system of claim 1 further comprising:
- a gripping subsystem configured to secure the moldable material and align the thermal transfer mold with the heat source subsystem;
- a second activating motor configured to move the gripping subsystem toward and away from the heat source subsystem;
- the heat source subsystem comprises a heat block assembly; and
- a control subsystem configured to control a temperature of the heat block assembly.

22. The moldable material shaping system of claim 20 wherein:
- the portion of the thermal transfer mold further comprises the wall having a uniform wall thickness;
- the heat source subsystem is configured to stably control the heating of the portion of the thermal transfer mold within a temperature range of less than 5 degrees Fahrenheit for a temperature time period of greater than 5 seconds; and
- the heat source subsystem is configured to uniformly control the heating of the portion of the thermal transfer mold within a temperature uniformity range such that a temperature in degrees Fahrenheit at one point of the thermal transfer mold is no greater than 20% from a temperature in degrees Fahrenheit of all other points of the thermal transfer mold.

\* \* \* \* \*